(12) United States Patent
Wu et al.

(10) Patent No.: US 10,950,026 B2
(45) Date of Patent: Mar. 16, 2021

(54) SYSTEMS AND METHODS FOR DISPLAYING A MEDICAL IMAGE

(71) Applicant: SHANGHAI UNITED IMAGING INTELLIGENCE CO., LTD., Shanghai (CN)

(72) Inventors: Dijia Wu, Shanghai (CN); Yaozong Gao, Shanghai (CN); Yiqiang Zhan, Shanghai (CN)

(73) Assignee: Shanghai United Imaging Intelligence Co., Ltd., Shanghai (CN)

(*) Notice: Subject to any disclaimer, the term of this patent is extended or adjusted under 35 U.S.C. 154(b) by 0 days.

(21) Appl. No.: 16/502,676

(22) Filed: Jul. 3, 2019

(65) Prior Publication Data
US 2020/0074712 A1   Mar. 5, 2020

(30) Foreign Application Priority Data

Aug. 31, 2018   (CN) .......................... 201811015393.8
Nov. 5, 2018    (CN) .......................... 201811306115.8

(51) Int. Cl.
*G06T 13/80*     (2011.01)
*G06K 9/32*      (2006.01)
(Continued)

(52) U.S. Cl.
CPC ............ *G06T 13/80* (2013.01); *G06K 9/3233* (2013.01); *G06N 3/08* (2013.01); *G06T 3/60* (2013.01);
(Continued)

(58) Field of Classification Search
None
See application file for complete search history.

(56) References Cited

U.S. PATENT DOCUMENTS

2002/0065460 A1   5/2002  Murao
2004/0236424 A1*  11/2004 Berez ...................... A61F 2/46
                                                      623/14.12
(Continued)

FOREIGN PATENT DOCUMENTS

CN   101216938 A   7/2008
CN   106780715 A   5/2017
(Continued)

OTHER PUBLICATIONS

Chinese Patent Office, Office Action dated Sep. 23, 2019, in Application No. 201811306115.8.
(Continued)

*Primary Examiner* — David H Chu
(74) *Attorney, Agent, or Firm* — Faegre Drinker Biddle & Reath LLP

(57) ABSTRACT

Method and system for displaying a medical image. For example, a computer-implemented method for displaying a medical image includes acquiring an original image of a target; obtaining a lesion region in the original image; selecting a region of interest in the original image based on at least the lesion region, the region of interest including the lesion region; obtaining a plurality of planar images of the region of interest from the original image of the target based on at least a predetermined setting; generating an animated display by grouping the plurality of planar images based on at least a predetermined order; and displaying the animated display related to the region of interest including the lesion region.

14 Claims, 19 Drawing Sheets

(51) Int. Cl.
*G06T 7/00* (2017.01)
*G06N 3/08* (2006.01)
*G16H 30/40* (2018.01)
*G06T 3/60* (2006.01)

(52) U.S. Cl.
CPC .......... *G06T 7/0012* (2013.01); *G16H 30/40* (2018.01); *G06T 2207/20081* (2013.01); *G06T 2207/30096* (2013.01); *G06T 2210/41* (2013.01)

(56) References Cited

U.S. PATENT DOCUMENTS

| | | | |
|---|---|---|---|
| 2007/0279435 A1 | 12/2007 | Ng et al. | |
| 2009/0087045 A1* | 4/2009 | Partain | G06T 7/11 382/128 |
| 2011/0116699 A1* | 5/2011 | Roy | G06T 5/10 382/131 |
| 2013/0257910 A1* | 10/2013 | Park | G06T 7/0012 345/672 |
| 2013/0322717 A1* | 12/2013 | Bar-Shalev | G06T 7/74 382/131 |
| 2015/0084625 A1* | 3/2015 | Yin | G01R 33/58 324/300 |
| 2017/0024883 A1* | 1/2017 | Urabe | A61B 8/463 |
| 2017/0046826 A1* | 2/2017 | Konen | G01R 33/4835 |
| 2019/0066343 A1* | 2/2019 | Bogoni | G06T 7/11 |
| 2019/0102878 A1* | 4/2019 | Zhang | G16H 50/20 |
| 2019/0131012 A1* | 5/2019 | Osawa | G06T 7/0012 |
| 2019/0236782 A1* | 8/2019 | Amit | A61B 10/0041 |

FOREIGN PATENT DOCUMENTS

| | | |
|---|---|---|
| CN | 107563378 A | 1/2018 |
| CN | 107595390 A | 1/2018 |

OTHER PUBLICATIONS

Chinese Patent Office, Office Action dated Dec. 18, 2019, in Application No. 201811306115.8.

Yang et al. (editors), excerpt from "HRCT Chest and Abdomen Disease Diagnosis," Tianjin City: Tianjin Science and Technology Press, published Jul. 31, 2007 (pp. 8-11). (In Chinese).

* cited by examiner

SYSTEMS AND METHODS FOR DISPLAYING A MEDICAL IMAGE

CROSS-REFERENCES TO RELATED APPLICATIONS

This application claims priority to Chinese Patent Application No. 201811306115.8, filed Nov. 5, 2018, and Chinese Patent Application No. 201811015393.8, filed Aug. 31, 2018, both of the above applications being incorporated by reference herein for all purposes.

BACKGROUND OF THE INVENTION

Certain embodiments of the present invention are directed to image processing. More particularly, some embodiments of the invention provide systems and methods for displaying a medical image. Merely by way of example, some embodiments of the invention have been applied to diagnosing a lesion in a medical image. But it would be recognized that the invention has a much broader range of applicability.

A medical imaging device refers to various instruments that use various media as an information carrier to reproduce a structure inside a human body as an image. Computerized tomography (CT) is a device that uses a precisely collimated X-ray beam, gamma ray, ultrasound, etc., together with a highly sensitive detector to scan a section of the human body one after another, and to generate a medical image. In order to obtain an image of a specific part of the patient, the patient can be scanned by a CT scanner to generate scan data. A sequence of images is generated from the scanned data. The sequence of images includes a plurality of slice images, each of which represents a cross-sectional image of the patient. A three-dimensional image of the patient is then generated from the sequence of images. The cross-sectional image can also be reconstructed by computer software to obtain a multi-planar cross-sectional image required for diagnosis, such as a coronal, sagittal, oblique, curved surface, etc. A doctor may then determine a lesion region (or area) of the patient by observing the sequence of images and/or the three-dimensional image.

Current conventional techniques, when radiologists detect and locate certain lesions, such as the detection and positioning of pulmonary nodules and rib fractures, it is common to observe tens to hundreds of layers of the patient's sequence of images. A doctor may manually scroll through the suspected lesion areas (or regions) in the tens to hundreds of layers of the sequence of images, and repeatedly observing and obtaining enough relevant contextual information to finally determine the diagnosis of the lesion. Such repeated scrolling of the images attributes to increased workload of the doctor. Thus, methods and systems for displaying a medical image that are more efficient are desired to reduce the workload and diagnosis time of a doctor.

BRIEF SUMMARY OF THE INVENTION

Certain embodiments of the present invention are directed to image processing. More particularly, some embodiments of the invention provide systems and methods for displaying a medical image. Merely by way of example, some embodiments of the invention have been applied to diagnosing a lesion in a medical image. But it would be recognized that the invention has a much broader range of applicability.

According to various embodiments, a computer-implemented method for displaying a medical image includes: acquiring an original image of a target; obtaining a lesion region in the original image; selecting a region of interest in the original image based on at least the lesion region, the region of interest including the lesion region; obtaining a plurality of planar images of the region of interest from the original image of the target based on at least a predetermined setting; generating an animated display by grouping the plurality of planar images based on at least a predetermined order; and displaying the animated display related to the region of interest including the lesion region.

In some embodiments, the obtaining a lesion region in the original image includes obtaining the lesion region by inputting the original image into a neural network trained by a set of training images. In certain embodiments, the obtaining a plurality of planar images of the region of interest from the original image of the target includes sequentially obtaining the plurality of planar images along a predetermined direction, the plurality of planar images being perpendicular to the predetermined direction.

In some embodiments, the obtaining a plurality of planar images of the region of interest from the original image of the target includes: establishing a Cartesian coordinate system including an X-axis, a Y-axis, and a Z-axis; performing a maximum intensity projection on the region of interest along the Z-axis in a first direction to obtain a first planar image of the plurality of planar images; rotating the Z-axis from the first direction to a second direction by a predetermined angle; and performing the maximum intensity projection on the region of interest along the Z-axis in the second direction to obtain a second planar image of the plurality of planar images. In certain embodiments, the obtaining a plurality of planar images of the region of interest from the original image of the target further includes: repeating at least rotating the Z-axis by the predetermined angle and performing the maximum intensity projection on the region of interest along the Z-axis to obtain another planar image of the plurality of planar images until the Z-axis is rotated back to the first direction.

In some embodiments, the repeating at least rotating the Z-axis by the predetermined angle and performing the maximum intensity projection on the region of interest along the Z-axis includes: fixing the Y-axis, rotating the X-axis about the Y-axis, and performing the maximum intensity projection on the region of interest; and fixing the X-axis, rotating the Y-axis about the X-axis, and performing the maximum intensity projection on the region of interest. In certain embodiments, the rotating the Z-axis from the first direction to a second direction by a predetermined angle includes fixing the Y-axis; and rotating the X-axis about the Y-axis from an initial direction in a predetermined direction. The various embodiments, the predetermined direction is clockwise or counterclockwise.

In some embodiments, the obtaining a plurality of planar images of the region of interest from the original image of the target further includes: repeating at least rotating the X-axis about the Y-axis until the X-axis is rotated back to the initial direction. In certain embodiments, the predetermined order is the same as an acquisition order by which the plurality of planar images have been obtained. In some embodiments, the predetermined order is a reverse of an acquisition order by which the plurality of planar images have been obtained.

In various embodiments, a medical image displaying device includes: an original image acquiring module configured to acquire an original image of a target; a lesion region obtaining module configured to obtain a lesion region in the original image; a region of interest selecting module configured to select a region of interest in the original image based on at least the lesion region, the region of interest including the lesion region; a planar image obtaining module configured to obtain a plurality of planar images of the region of interest from the original image of the target based on at least a predetermined setting; an animated display generating module configured to generate an animated display by grouping the plurality of planar images based on at least a predetermined order; and a displaying module configured to display the animated display related to the region of interest including the lesion region.

In some embodiments, the planar image obtaining module is further configured to sequentially obtain the plurality of planar images along a predetermined direction, the plurality of planar images being perpendicular to the predetermined direction.

In certain embodiments, the planar image obtaining module is further configured to: establish a Cartesian coordinate system including an X-axis, a Y-axis, and a Z-axis; perform a maximum intensity projection on the region of interest along the Z-axis in a first direction to obtain a first planar image of the plurality of planar images; rotate the Z-axis from the first direction to a second direction by a predetermined angle; and perform the maximum intensity projection on the region of interest along the Z-axis in the second direction to obtain a second planar image of the plurality of planar images.

In some embodiments, the planar image obtaining module is further configured to repeat at least rotating the Z-axis by the predetermined angle and performing the maximum intensity projection on the region of interest along the Z-axis to obtain another planar image of the plurality of planar images until the Z-axis is rotated back to the first direction. In various embodiments, the predetermined order is the same as an acquisition order by which the plurality of planar images have been obtained. In certain embodiments, the predetermined order is a reverse of an acquisition order by which the plurality of planar images have been obtained.

In some embodiments, a non-transitory computer-readable medium with instructions stored thereon, that when executed by a processor, perform the processes including: acquiring an original image of a target; obtaining a lesion region in the original image; selecting a region of interest in the original image based on at least the lesion region, the region of interest including the lesion region; obtaining a plurality of planar images of the region of interest from the original image of the target based on at least a predetermined setting; generating an animated display by grouping the plurality of planar images based on at least a predetermined order; and displaying the animated display related to the region of interest including the lesion region.

In certain embodiments, the non-transitory computer-readable medium with instructions stored thereon, that when executed by a processor, perform the process: sequentially obtaining the plurality of planar images along a predetermined direction, the plurality of planar images being perpendicular to the predetermined direction.

In certain embodiments, the non-transitory computer-readable medium with instructions stored thereon, that when executed by a processor, perform the processes: establishing a Cartesian coordinate system including an X-axis, a Y-axis, and a Z-axis; performing a maximum intensity projection on the region of interest along the Z-axis in a first direction to obtain a first planar image of the plurality of planar images; rotating the Z-axis from the first direction to a second direction by a predetermined angle; and performing the maximum intensity projection on the region of interest along the Z-axis in the second direction to obtain a second planar image of the plurality of planar images.

Depending upon embodiment, one or more benefits may be achieved. These benefits and various additional objects, features and advantages of the present invention can be fully appreciated with reference to the detailed description and accompanying drawings that follow.

DETAILED DESCRIPTION OF THE INVENTION

Figure 1:
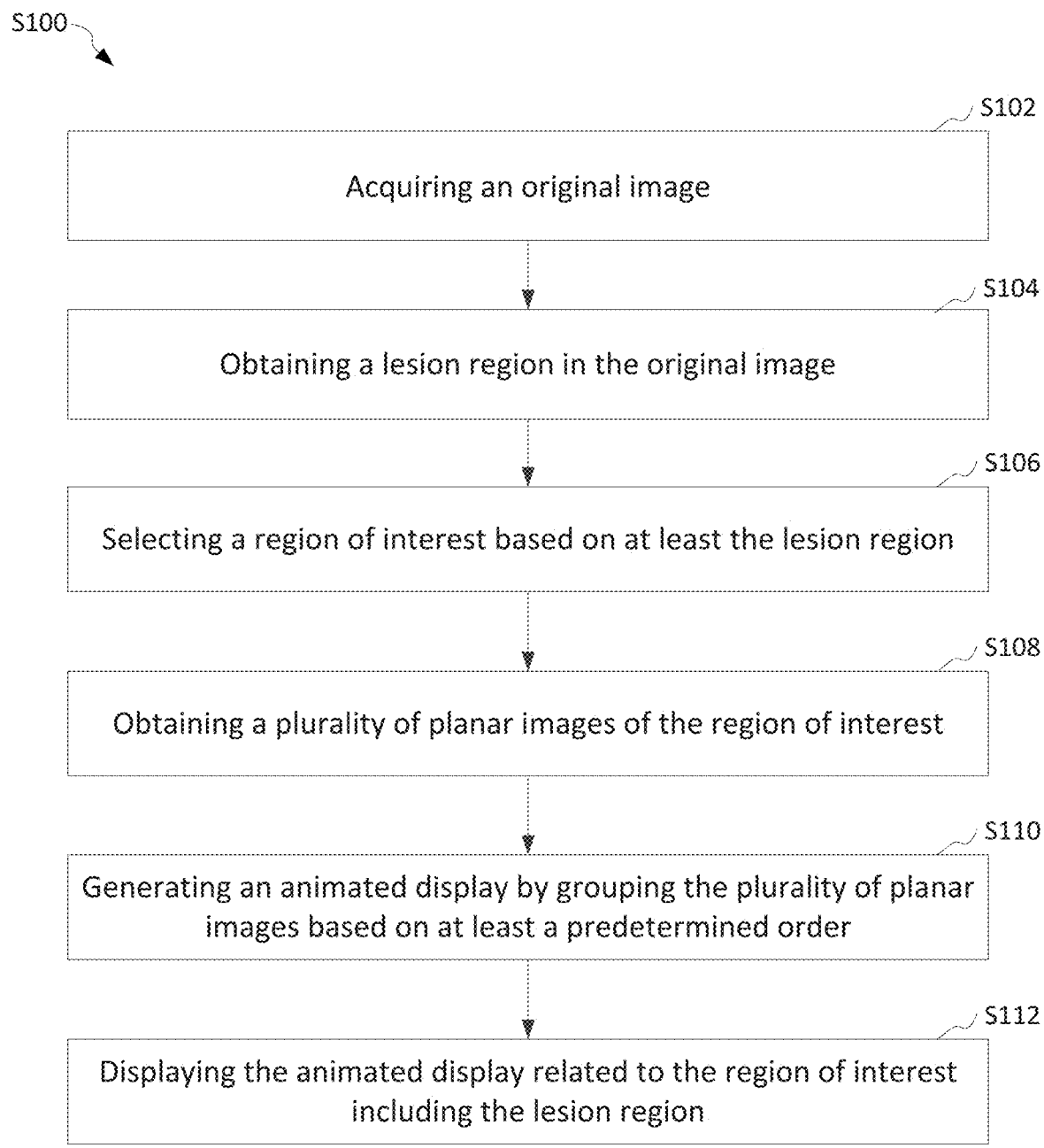
FIG. 1 is a simplified diagram showing a method for displaying a medical image, according to some embodiments of the present invention.

Certain embodiments of the present invention are directed to image processing. More particularly, some embodiments of the invention provide systems and methods for displaying a medical image. Merely by way of example, some embodiments of the invention have been applied to diagnosing a lesion in a medical image. But it would be recognized that the invention has a much broader range of applicability.

The present application relates to the field of medical image technology, and in particular, to a method, a displaying device, a computer device, and a storage medium, for displaying a medical image.

In various embodiments, a method for displaying a medical image includes acquiring (e.g., capturing or receiving) an original image of an object of interest, selecting a lesion region in the original image, selecting a region of the original image based on the lesion region as a region of interest, acquiring a plurality of planar images of the original image in the region of interest according to a preset acquisition setting; generating an animated image according to a preset sequence, and displaying the animated image from a preset viewpoint.

In some embodiments, the selecting a lesion region in the original image includes inputting the original image into a neural network trained based on at least a training set of training images to obtain the lesion region.

In some embodiments, the acquiring a plurality of planar images of the original image in the region of interest according to a preset acquisition setting includes sequentially slicing the plurality of planar images of the original image in the region of interest along a preset direction and perpendicularly to the present direction.

In some embodiments, the acquiring a plurality of planar images of the original image in the region of interest according to a preset acquisition setting includes establishing a three-dimensional Cartesian coordinate system in the region of interest, performing a maximum intensity projection on the region of interest from an initial position along the Z-axis direction of the Cartesian coordinate system to obtain a first planar image of the plurality of planar images, repeatedly rotating the original image including the region of interest according to a preset rotational direction by a preset rotational angle, repeatedly performing the maximum density projection on the region of interest along the Z-axis direction to obtain another planar image of the plurality of planar images after every rotation in the present rotational direction by the preset rotational angle, wherein the rotating the original image is repeated until the region of interest returns to the initial position.

In some embodiments, the repeatedly rotating the original image including the region of interest according to a preset direction by a preset angle, repeatedly performing the maximum density projection on the region of interest along the Z-axis direction to obtain another planar image of the plurality of planar images after every rotation in the present rotational direction by the preset rotational angle, wherein the rotating the original image is repeated until the region of interest returns to the initial position includes rotating the region of interest about the Y-axis in the preset direction by the preset angle, performing the maximum intensity projection on the region of interest along the Z-axis direction to obtain another planar image of the plurality of planar images after each rotation about the Y-axis, rotating the region of interest about the X-axis in the preset direction by the preset angle, performing the maximum intensity projection on the region of interest along the Z-axis direction to obtain another planar image of the plurality of planar images after each rotation about the X-axis, wherein the rotating the region of interest about the Y-axis and rotating the region of interest about the X-axis are alternatingly performed until the region of interest is rotated back to the initial position. In some embodiments, the preset direction is clockwise or counter-clockwise.

In some embodiments, the generating an animated image according to a preset sequence includes generating the animated image in a sequence identical to the sequence in which the plurality of planar images were obtained or in a sequence being the reverse of the sequence in which the plurality of planar images were obtained.

In some embodiments, a medical image viewing device includes an original image acquiring module, a lesion region selecting module, a region of interest selecting module, a planar image acquiring module, an animated image generating module, and a displaying module. The original image acquiring module is configured to acquire (e.g., capturing or receiving) an original image of an object of interest. The lesion region selecting module is configured to select a lesion region in the original image. The region of interest selecting module is configured to select a region of the original image based on the lesion region as a region of interest. The planar image acquiring module is configured to acquire a plurality of planar images of the original image in the region of interest according to a preset acquisition setting. The animated image generating module is configured to generate an animated image according to a preset sequence. The displaying module is configured to display the animated image from a preset viewpoint.

In some embodiments, a computer apparatus includes a memory and a processor, the memory storing a computer-executable program, wherein the processor, when the computer-executable program is executed, implements the processes of any of the methods described above. In some embodiments, a computer-readable non-transitory storage medium having stored thereon a computer-executable program, wherein the computer-executable program, when executed by a processor, implements the processes of any of the methods described above.

In various embodiments, the medical image display method, the viewing device, the computer device and the storage medium for acquiring (e.g., capturing or receiving) an original image of an object of interest, selecting a lesion region in the original image, selecting a region of the original image based on the lesion region as a region of interest, acquiring a plurality of planar images of the original image in the region of interest according to a preset acquisition setting; generating an animated image according to a preset sequence, and displaying the animated image from a preset viewpoint, help a doctor to determine a lesion within the original image in reduced time and reduced workload by observing the animated image. An animated display may be referred to as an animated image, animation, animated video, dynamic image, dynamic video, or a dynamic display.

According to some examples, the reference numerals in the drawings of the present disclosure are used as followed: 100 is an original image obtaining module, 200 is a lesion region (or area) selecting module, 300 is a region of interest selecting module, 400 is a planar image acquiring module, 410 is a slicing unit, 420 is a coordinate system establishing unit, and 430 is a maximum intensity projecting unit (initial position), 440 is a rotating unit, 441 is an X-axis rotating sub-unit, 442 is a Y-axis rotating sub-unit, 443 is a planar image acquiring sub-unit, 500 is an animated image generating module, and 600 is a displaying module.

In order to make the objects, technical solutions, and advantages of the present application more comprehensible, the present application will be further described in detail below with reference to the accompanying drawings and embodiments. It is understood that the specific embodiments described herein are merely illustrative of the application and are not intended to be limiting.

In some embodiments, scanning of a scanned object to obtain a medical image of the scanned object is done via a medical imaging device, wherein the scanned object may be a patient's whole-body organ, or an organ, a tissue or a collection of cells that are the focus of an examination. In certain embodiments, the scanning of a scanned object includes obtaining scan data and generating a sequence of medical images based on the scan data. For example, the sequence of medical images is a collection of images each obtained by taking the cross section of the scanning object in a scanning direction. In some embodiments, generating of a three-dimensional (3D) image (e.g., of the internal structure of the scanned object) includes compiling (e.g., stacking) the sequence of medical images in an order (e.g., same or reverse of the sequence in which the medical images are taken). In certain examples, the medical imaging device is an X-ray imaging instrument, a computed tomography instrument (e.g., common CT, spiral CT), a positron emission tomography instrument (PET), a magnetic resonance imaging (MR) instrument, an infrared scanning device, or a combined scanning device.

FIG. 1 is a simplified diagram showing a method S100 for displaying a medical image, according to some embodiments of the present invention. This diagram is merely an example, which should not unduly limit the scope of the claims. One of ordinary skill in the art would recognize many variations, alternatives, and modifications. The method S100 includes a process S102 of acquiring an original image, a process S104 of obtaining a lesion region in the original image, a process S106 of selecting a region of interest based on at least the lesion region, a process S108 of obtaining a plurality of planar images of the region of interest, a process S110 of generating an animated display by grouping the plurality of planar images based on at least a predetermined order, and/or a process S112 of displaying the animated display related to the region of interest including the lesion region. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In some embodiments, the process S102 of acquiring an original image includes scanning (e.g., with a medical imaging device) a target (e.g., an object, an object of interest) based on at least a predetermined (or preset) setting (or a set of parameters). In certain examples, acquiring the original image includes acquiring a three-dimensional image as the original image. In some examples, the acquiring the three-dimensional image includes generating the three-dimensional image based on at least a plurality of images (e.g., 2-dimensional, planar) obtained by scanning the target using the medical imaging device. In various examples, the target (e.g., the scanning object) is a whole-body organ of a human or an animal, an organ, a tissue or a collection of cells of the human or animal. In certain embodiments, the process S102 of acquiring an original image includes receiving (e.g., from an internal memory or an external memory) a pre-captured image (e.g., a 3D image) and using the pre-captured image as the original image.

In some embodiments, the process S104 of obtaining a lesion region (e.g., three-dimensional) in the original image (e.g., three-dimensional) includes inputting the original image into a neural network, such as a neural network trained based on at least a training set of training images. For example, the neural network is configured to determine, select, or obtain a lesion region in the original image, such as automatically, based on at least data (e.g., big data) analysis. In certain embodiments, the lesion region is selected to include one or more candidates of fractured bones and/or diseased tissues, such as ones having pathogenic microorganisms. For example, a lesion region (or area) includes a part of a lung that is destroyed by tuberculosis. In various embodiments, the neural network is trained based on at least machine learning, such as trained based on at least learning features and/or variables indicative of a lesion, to help select one or more lesion regions in an image (e.g., the original image). For example, features and variables indicative of a lesion are learnt by training the neural network using the set of training images including a plurality of two-dimensional images and/or three-dimensional images (e.g., obtained by a medical imaging device).

In some examples, inputting the original image into the neural network (e.g., trained neural network) to obtain the lesion region is based on at least selecting or extracting a region of the original image including features and/or variables matching the learnt features and/or indicative of a lesion. In certain examples, the neural network is trained to select one or more lesion regions in an image (e.g., original image) and to output one or more coordinates of the one or more lesion regions in the image. For example, the neural network is trained to establish a 3-dimensional Cartesian coordinate system (e.g., in the original image) and assigning a (x, y, z) coordinate position to each selected lesion region. In certain embodiments, obtaining the lesion region in the original image includes receiving user input (e.g., from a doctor), such as a coordinate determined by a user, and selecting a lesion region based on at least the user input. In some examples, the lesion region is displayed as highlighted, marked, labeled, annotated, outlined, and/or bounded in the original image when displayed (e.g., in the process S112). For example, the lesion region is surrounded by a bounding box, such as in the original image when displayed.

In various embodiments, the process S106 of selecting a region of interest based on at least the lesion region includes selecting one or more region of interests based on (e.g., to include) at least one or more lesion regions determined in the process S104. For example, selection a region of interest minimizes selecting regions of the original image that are substantially unrelated to any lesion and/or contextual region useful for diagnosing a lesion. In yet another example, the region of interest equals to the lesion region. In certain examples, the selecting a region of interest based on at least the lesion region includes selecting a region to include the lesion region at the center and sufficient relevant contextual region around or near the lesion region. In some examples, including relevant contextual region in the region of interest helps identifying lesion size and relative position of the lesion region in respect to one or more features (e.g., a rib) in the original image. In various examples, the contextual region helps a user to confirm the lesion region identified is accurate.

In various embodiments, the process S108 of obtaining a plurality of planar images of the region of interest includes obtaining (e.g., acquiring) each planar image of the plurality of planar images perpendicularly to a predetermined (preset) direction along the predetermined direction. In certain examples, obtaining the plurality of planar images includes taking a plurality of cross-sectional planar images of the region of interest selected in the process S106 or of the lesion region in the process S104. In some examples, at least one planar image of the plurality of planar images are obtained in the sagittal plane or in the coronal plane of the region of interest. In certain examples, at least one planar image of the plurality of planar images are obtained along a line (e.g., any line) from one end to another end of the region of interest. In some examples, a planar image includes a tomographic image, an anatomical image, a slice image of a three-dimensional image.

In various examples, obtaining the plurality of planar images includes establishing a coordinate system, three-dimensional coordinate system, such as a Cartesian coordinate system, in the lesion region, the region of interest, and/or in the original image. The Cartesian coordinate system includes an X-axis, a Y-axis, and a Z-axis, each established orthogonally to each other. In some embodiments, obtaining the plurality of planar images includes performing a maximum intensity projection on the region of interest (e.g., including the lesion region) along the Z-axis direction from an initial position to obtain a first planar image of the plurality of planar images.

In some examples, establishing the Cartesian coordinate system includes establishing the coordinate system in respect to a scanning platform (e.g., a bed) of the medical imaging device. For example, establishing the Cartesian coordinate system includes establishing the x-axis from left-to-right of the scanning platform, the y-axis from top-to-bottom of the scanning platform, and z-axis from head-to-foot, of the scanning platform. In some embodiments, establishing the Cartesian coordinate system is based on at least features of the original image, such as based on a rib. For example, establishing the Cartesian coordinate system includes establishing an X-Y-plane based on at least a plane defined by a central axis of the rib and establishing the Z-axis based on at least the normal vector of the X-Y-plane.

In certain examples, obtaining the plurality of planar images includes repeatedly rotating the region of interest in the predetermined direction by a predetermined angle until the region of interest returns to an initial position. In various examples, obtaining the plurality of planar images includes performing the maximum intensity projection on the region of interest along the Z-axis direction after each rotating of the region of interest in the predetermined direction by the predetermined angle to obtain another planar image of the plurality of planar images. In some embodiments, instead of rotating the region of interest in respect to the coordinate system, obtaining the plurality of planar images includes rotating the coordinate system in respect to the region of interest. In such embodiments, maximum intensity projection is performed after each rotating of the coordinate system until the coordinate system returns to a first (or initial) position (or orientation). In some examples, the first position is the position of the region of interest or the coordinate system when the coordinate system is established. In certain embodiments, the first position is a relative position between the region of interest and the coordinate system when the coordinate system is established.

In various embodiments, the process S110 of generating an animated display (or animated image) by grouping the plurality of planar images based on at least a predetermined order includes generating the animated display by grouping the plurality of planar images based on at least an order identical to the sequence in which the plurality of planar images is obtained or based on at least an order reverse to the sequence in which the plurality of planar images is obtained. In some examples, when the plurality of planar images is obtained by taking cross-sectional images, the sequence in which the plurality of planar images is obtained is from a first end of the region of interest to a second end of the region of interest opposite from the first end. For example, the first end and the second end of the region of interest defines a thickness, wherein the sequence in which the plurality of planar images is obtained is along the thickness of the region of interest. In various embodiments, when the plurality of planar images is obtained by rotating the region of interest or by rotating the coordinate system, and performing the maximum intensity projection on the region of interest along the Z-axis, the sequence in which the plurality of planar images is obtained is from an initial position (e.g., of the region of interest or of the coordinate system) along a predetermined direction (e.g., clockwise or counterclockwise) and back to the initial position. In certain embodiments, generating the animated display includes inputting the plurality of planar images into a video encoder to be processed (e.g., compressed) into a video format (e.g., MPEG4, H.264) or into an interchange file format (e.g., GIF).

In various embodiments, the process S112 of displaying the animated display related to the region of interest including the lesion region includes displaying the animated display via a display interface, such as a display interface of a CT system. In certain examples, displaying the animated display includes displaying a plurality of animated displays in a plurality of display windows (e.g., cells) in a display interface (e.g., a monitor, a screen). For example, the process S112 includes displaying each of the display of animated displays in one of the plurality of display windows. In some examples, displaying the animated display includes displaying a reconstructed image (e.g., a three-dimensional, multi-planar, and/or multi-surface image) including one or more reconstructed surfaces (e.g., curved surfaces) of a feature, an object, and/or a structure (e.g., a rib) in the region of interest. In certain embodiments, displaying the animated display includes displaying one or more planar (e.g., two-dimensional) images corresponding to the reconstructed image (e.g., three-dimensional). For example, one or more planar images includes at least one cross-sectional image of the feature, object, or structure in the region of interest. In some examples, at least one of the plurality of display windows is a floating window configured to display an animated display. In various examples, at least some display windows of the plurality of display windows are linked, such that when one of the linked display window is manipulated, the rest of the linked display windows are modified in response to the manipulation.

In certain examples, the process S112 of displaying the animated display includes receiving user input (e.g., from a physician), such as dynamically (e.g., in real-time) receiving user input and displaying one or more adjusted animated display in response to the user input. For example, displaying one or more adjusted animated displays includes generating the one or more adjusted animated displays based on at least performing one or more of processes S102, S104, S106, S108 and S110 based on at least the received user input. In certain examples, receiving user input includes receiving one or more preferences and/or settings (e.g., viewing habits, threshold values, default values, target values), which, in some examples, helps improve diagnostic efficiency and/or accuracy. In some examples, receiving user input includes receiving an adjustment command of one of a plurality of linked display windows for applying a display adjustment to the plurality of linked display windows. In various examples, receiving user input includes receiving a display speed, a forward, rewind, speed up, slow down, loop, and/or pause instruction to be applied to the animated display.

In various embodiments, the method for displaying a medical image includes acquiring (e.g., capturing or receiving) an original image of an object of interest, selecting a lesion region in the original image, selecting a region of the original image based on the lesion region as a region of interest, acquiring a plurality of planar images of the original image in the region of interest according to a preset acquisition setting; generating an animated image according to a preset sequence, and displaying the animated image from a preset viewpoint. In some examples, the method described helps a doctor to determine a lesion within the original image in reduced time and reduced workload by observing the animated image.

Figure 2:
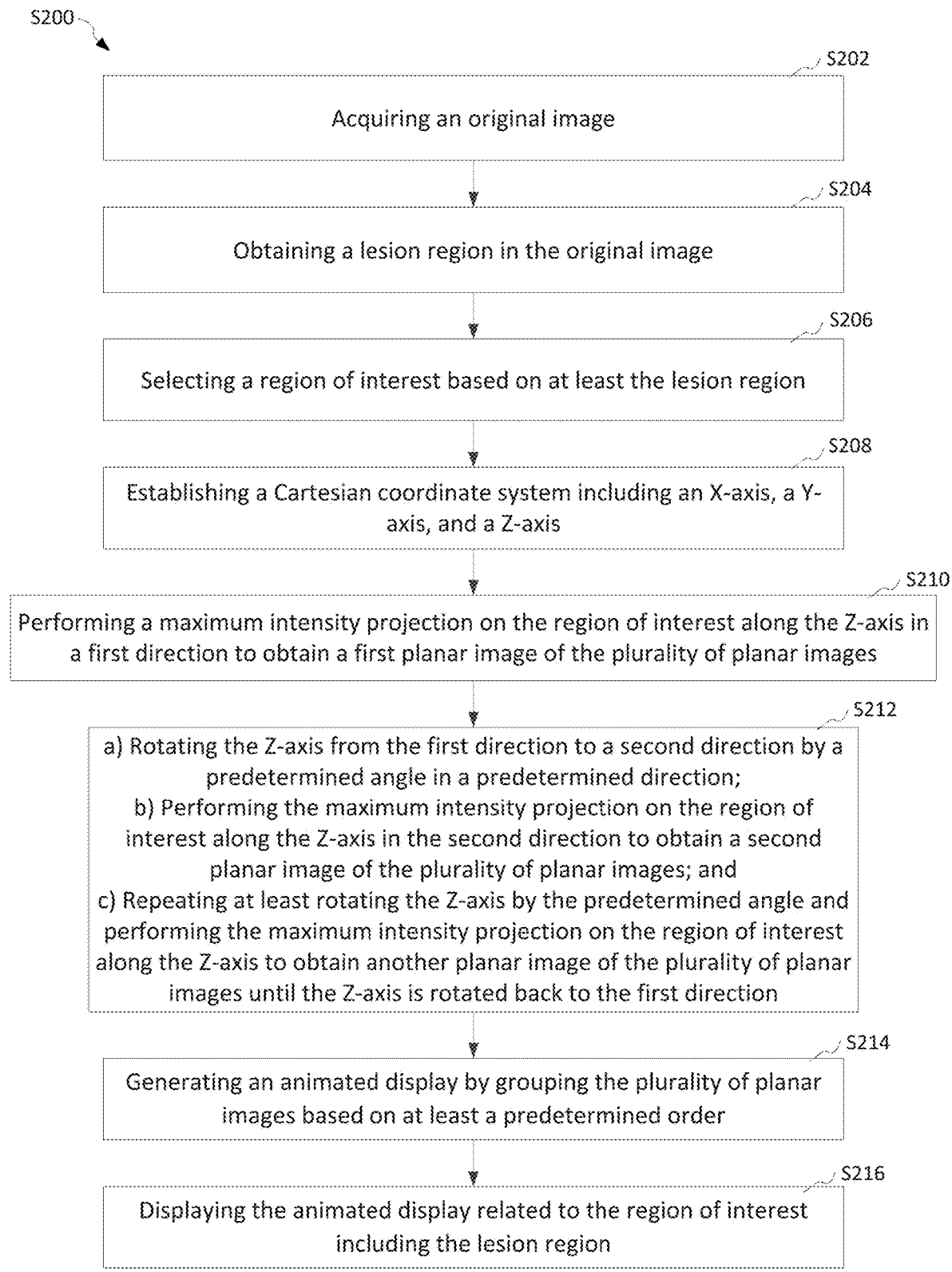
FIG. 2 is a simplified diagram showing another method for displaying a medical image, according to some embodiments of the present invention.

FIG. 2 is a simplified diagram showing another method S200 for displaying a medical image, according to some embodiments of the present invention. This diagram is merely an example, which should not unduly limit the scope of the claims. One of ordinary skill in the art would recognize many variations, alternatives, and modifications. In some embodiments, the method S200 for displaying a medical image includes a process S202 of acquiring an original image, a process S204 of obtaining a lesion region in the original image, a process S206 of selecting a region of interest based on at least the lesion region, a process S208 of establishing a Cartesian coordinate system including an X-axis, a Y-axis, and a Z-axis, a process S210 of performing a maximum intensity projection on the region of interest along the Z-axis in a first direction to obtain a first planar image of the plurality of planar images, a process S212 of rotating the Z-axis from the first direction to a second direction by a predetermined angle in a predetermined direction, performing the maximum intensity projection on the region of interest along the Z-axis in the second direction to obtain a second planar image of the plurality of planar images, and repeating at least rotating the Z-axis by the predetermined angle in the predetermined direction and performing the maximum intensity projection on the region of interest along the Z-axis to obtain another planar image of the plurality of planar images until the Z-axis is rotated back to the first direction, a process S214 of generating an animated display by grouping the plurality of planar images based on at least a predetermined order, and/or a process S216 of displaying the animated display related to the region of interest including the lesion region. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In certain embodiments, a method for displaying a medical image includes acquiring the original image, selecting a lesion region in the original image, selecting a region of interest based on the lesion region, establishing a Cartesian coordinate system, performing the maximum intensity projection at an initial position along the Z-axis direction to obtain a maximum intensity projection as a first planar image of a plurality of planar images, repeatedly rotating the region of interest in a preset direction by a preset angle until the region of interest is rotated back to the initial position, performing the maximum intensity projection along the Z-axis following each rotation of the region of interest to obtain another maximum intensity projection as another planar image of the plurality of planar images, generating an animated display (or image) by grouping the plurality of planar images based on at least a predetermined order, and displaying the animated display related to the region of interest including the lesion region. In various examples, the animated display helps a physician to more efficiently, effectively, and/or clearly observe a lesion region.

In various embodiments, the method S200 includes a process S202 of acquiring an original image of the detected object. In certain examples, the process S202 includes acquiring an original image using a medical imaging device to scan a target (e.g., detected) object, such as according to a preset scan parameter, to obtain an image (e.g., three-dimensional) of the scanned object, which is used as the original image. The scanning object may be a whole-body organ of a human or an animal, or may be an organ, a tissue or a collection of cells.

In various embodiments, the method S200 includes a process S204 of selecting a lesion region in the original image. In some examples, the lesion region includes a diseased tissue having a pathogenic microorganism. For example, the lesion region includes a part of the lung that is destroyed by tubercle bacillus, a fractured region of a rib, a narrow part of a patient's tubular structure (e.g., blood vessels, trachea), and/or a calcification point in the mammary gland.

In some embodiments, the process S204 of obtaining a lesion region in the original image includes inputting the original image into a neural network, such as a neural network trained based on at least a set of training images. For example, the neural network is configured to determine, select, or obtain a lesion region in the original image, such as automatically, based on at least data analysis (e.g., big data analysis). In certain embodiments, the lesion region is selected to include one or more candidates of fractured bones and/or diseased tissues, such as ones having pathogenic microorganisms. For example, a lesion region (or area) includes a part of a lung that is destroyed by tuberculosis. In various embodiments, the neural network is trained based on at least machine learning, such as trained based on at least learning features and/or variables indicative of a lesion, to help select one or more lesion regions in an image (e.g., original image). For example, features and variables indicative of a lesion are learnt by training the neural network using the set of training images including a plurality of two-dimensional images and/or three-dimensional images (e.g., obtained by a medical imaging device).

In some examples, inputting the original image into the neural network (e.g., trained neural network) to obtain the lesion region is based on at least selecting or extracting a region of the original image including features and/or variables matching the learnt features and/or indicative of a lesion. In certain examples, the neural network is trained to select one or more lesion regions in an image (e.g., original image) and to output one or more coordinates of the one or more lesion regions in the image. For example, the neural network is trained to establish a 3-dimensional Cartesian coordinate system (e.g., in the original image) and assigning a (x, y, z) coordinate position to each selected lesion region. In certain embodiments, obtaining the lesion region in the original image includes receiving user input (e.g., from a doctor), such as a coordinate determined by a user, and selecting a lesion region based on at least the user input.

In certain embodiments, selecting a lesion region in an original image includes selecting a fracture region in a rib image, which includes obtaining the rib image, selecting a region of interest of the rib image including the fracture region, and selecting the fracture region based on at least a fracture detection model. For example, the fracture detection model is based on at least a convolutional neural network model (algorithm) that is trained for fracture detection.

In some examples, selecting a lesion region is based on at least a (deep) convolutional neural network model. The convolutional neural network model, according to some embodiments, includes a five-layer convolutional neural network model including: a first convolutional layer, a first pooling layer, a second convolutional layer, a second pooling layer, and a fully-connected layer, wherein in various embodiments, selecting a lesion region includes applying the convolutional neural network model to each planar image of the plurality of planar images, which includes the processes of (1) at the first convolutional layer, inputting a planar (slice) image into the first convolutional layer. In some examples, for a planar image with a size of 64×64, thirty-six 5×5-sized convolution kernels are used for pre-training to convolve the input planar image to obtain thirty-six 64×64-sized feature projections (a feature projection can also be referred to as a feature map or feature image);

(2) at the first pooling layer, pooling the thirty-six 64×64-sized feature projections using 3×3-sized windows to obtain thirty-six 32×32-sized feature projections;

(3) at the second convolutional layer, obtaining one or more 5×5-sized image blocks by sampling the thirty-six 32×32-sized feature projections, obtaining sixty-four 5×5-sized weights based on at least training the image blocks (e.g., the feature projections) using a sparse self-encoding network, using the weights as a convolution kernel, and using the convolution kernel to convolve the thirty-six 32×32-sized feature projections to obtain sixty-four 24×24-sized feature projections. In certain examples, every three projections of the thirty-six 32×32-sized feature projections are convolved twice, with the first convolution performed with the nearest neighboring projections and the second convolution performed with the second nearest neighboring projections, resulting one of the sixty-four 24×24-sized feature projections;

(4) at the second pooling layer, pooling the sixty-four 24×24-sized feature projections using 3×3-sized windows to obtain sixty-four 8×8-sized feature projections; and (5) at the fully-connected layer, generating a dictionary, which according to some examples, includes inputting a plurality of images (e.g., 1,300 images) into the first convolutional layer, the first pooling layer, the second convolutional layer, and the second pooling layer to obtain a network of feature projections at 1300×64×8×8 elements, which corresponds to obtaining sixty-four 8×8-sized projections for each of the 64×64-sized input image. In certain embodiments, generating the dictionary further includes reducing dimension, such as reducing 1300×64×8×8 to 83200×64 and outputting sixty-four sparse self-encoding networks to train the dictionary. An element may also be referred to as a feature value.

In some embodiments, the image processing method provided by the embodiment of the invention includes obtaining and selecting training samples (images) by processing one or more scanned (original) images (e.g., used as the source) including a rib. For example, the training samples includes positive training samples obtained from twenty-six patient's (subjects) in regions of the patients where a fractured bone is present. In certain examples, the training samples are obtained three-dimensionally (e.g., in a connected domain). In various embodiments, the training samples includes negative training samples (e.g., images) obtained in regions of the patients where no fractured bone is present. In certain embodiments, the positive training samples and the negative training samples combine into a plurality of training sample images (e.g., from about a hundred thousand to about one million sample images) In certain embodiments, obtaining a training sample image includes, from an obtained training sample image (e.g., a 2D slice image), rotate and/or translate to a new orientation to obtain the new training sample image. In some embodiments, a positive training sample image and/or a negative training sample image is a 32×32-sized or (32~64)×(32~64)-sized two-dimensional image. In various embodiments, the resolution of each of the training sample images is 0.25 mm or 0.2 mm-0.6 mm. In some examples, training is performed using original CT image parameters.

In various embodiments, the neural network configured to be trained is structured as follows: the neural network uses a convolutional neural network (CNN) and a stochastic gradient descent method (SGD) as an optimization algorithm for updating weights. In certain examples, the convolutional neural network has twelve layers, of which including a first convolutional layer, a second convolutional layer, a third convolutional layer, a first nonlinear projection layer (which may also be referred to as a nonlinear transformation layer, a nonlinear functional layer), a second nonlinear projection layer, a third nonlinear projection layer, a first pooling layer, a second pooling layer, a third pooling layer, a first fully-connected layer, a second fully-connected layer, and a Loss layer.

In various embodiments, the first network layer is the first convolutional layer for extracting one or more features from an input image and set sixty-four 5×5-sized convolution kernels. For example, in the first convolutional layer, the input image is convolved with the convolution kernels to obtain sixty-four 32×32-sized feature projections (or maps).

In various embodiments, the second network layer is the first nonlinear projection layer for adding nonlinearity and increasing convergence speed. For example, the feature projections from the first network layer is nonlinearly projected using a rectified linear unit function (e.g., Relu) to obtain a set of feature projections (or maps) of the second network layer.

In various embodiments, the third network layer is the first pooling layer for reducing image size and noise of the feature projections from the second network layer. For example, a pooling kernel is 3×3-sized and is used for pooling the feature projections of the second network layer. In certain embodiments, pooling is performed by taking the maximum value within the 3×3-sized windows. For example, the pooling obtains sixty-four 16×16-sized feature maps of the third network layer.

In various embodiments, the fourth network layer is the second convolutional layer, wherein, according to some examples, sixty-four 5×5-sized convolution kernels are set and used to obtain sixty-four 16×16-sized feature maps of the fourth network layer.

In various embodiments, the fifth network layer is the second nonlinear projection layer, wherein the sixty-four feature maps of the fourth network layer is nonlinearly projected using a rectified linear unit function (e.g., Relu) to obtain a set of feature projections (or maps) of the fifth network layer.

In various embodiments, the sixth network layer is the second pooling layer for pooling the feature projections of the fifth network layer to obtain (e.g., using 3×3-sized pooling kernels) a set (e.g., sixty-four) of feature maps (e.g., 8×8-sized) of the sixth network layer.

In various embodiments, the seventh network layer is the third convolutional layer for obtaining a set of feature maps on the seventh network layer by convolving the feature maps of the sixth network layer based one at least the (5×5-sized) convolution kernels.

In various embodiments, the eighth network layer is the third nonlinear projection layer for obtaining a set of feature maps of the eighth network layer by nonlinearly projecting the feature maps of the seventh network layer using a rectified linear unit function (e.g., Relu).

In various embodiments, the ninth network layer is the third pooling layer for pooling the feature projections of the eighth network layer to obtain (e.g., using 3×3-sized pooling kernels) a set (e.g., one-hundred-twenty-eight) of feature maps (e.g., 4×4-sized) of the ninth network layer.

In various embodiments, the tenth network layer is the first fully-connected layer for fully-connecting the feature maps of the ninth network layer based on at least a plurality of convolution kernels (e.g., one-hundred-twenty-eight). In some examples, each of the convolution kernel is 4×4-sized. In certain examples, fully-connecting the feature maps of the ninth network layer outputs a set of feature maps of the tenth network layer that are 1×1-sized.

In various embodiments, the eleventh network layer is the second fully-connected layer for fully-connecting the feature maps of the tenth network layer based on at least a plurality of convolution kernels (e.g., two). For example, each of the convolution kernel is 1×1-sized. In certain examples, fully-connecting the feature maps of the tenth network layer outputs a set of feature maps of the eleventh network layer.

In various embodiments, the twelfth network layer is the Loss layer for calculating the difference between a predicted value and the actual value. For example, calculating the difference includes returning one or more gradients based on at least a back propagation (BP) algorithm and updating one or more weights and/or biases for each layer.

In various embodiments, training the neural network includes repeatedly updating the one or more weights and/or biases for each layer based on at least one or more Loss values obtained from inputting the plurality of training sample images into the neural network. In certain embodiments, the one or more Loss values are obtained based on at least a training set (e.g., with unknown lesion diagnosis) and a verification set (e.g., with known lesion diagnosis) and are reduced continuously during the training process until the Loss value of the verification set no longer lowers, which is when the training is stopped to prevent over-fitting. Once the training is stopped, the trained neural network model is selected to be used as the (final) classifier for the neural network model. In some embodiments, during testing, the twelfth layer is replaced with a softmax layer for classifying the feature maps of the eleventh layer to obtain a diagnostic (or classification) result, such as a confidence level of a lesion determination.

In some embodiments, initialization of the neural network model includes constructing a neural network model based on at least a convolutional neural network (CNN) or a generated confrontation network (GAN). In some examples, a convolutional neural network (CNN) includes a SRCNN (Super-Resolution Convolutional Neural Network), a DnCNN (Denoising Convolutional Neural Network), a U-net, a V-Net, and/or a FCN (Fully Convolutional Network, full convolutional neural network). In some embodiments, the neural network model includes multiple layers, such as an input layer, multiple hidden layers, and an output layer. For example, the plurality of hidden layers includes one or more convolutional layers, one or more bulk normalization layers, one or more activation layers, a fully connected layer, a cost function layer, and the like. In certain examples, each of the plurality of layers includes a plurality of nodes.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

In various embodiments, the method S200 includes a process S206 of selecting a region of interest based on at least the lesion region includes selecting one or more region of interests based on one or more lesion regions determined in the process S204. For example, selection a region of interest minimizes selecting regions of the original image that is unrelated to any lesion and/or contextual region useful for diagnosing a lesion. In certain examples, the selecting a region of interest based on at least the lesion region includes selecting a region to include the lesion region at the center and sufficient relevant contextual region around the lesion region. In some examples, relevant contextual region helps identify lesion size and relative position of the lesion region in respect to one or more features in the original image. In various examples, the contextual region helps a user to confirm the lesion region identified is accurate.

In various embodiments, the method S200 includes a process S208 of establishing a Cartesian coordinate system including an X-axis, a Y-axis, and a Z-axis. In some examples, the Cartesian coordinate system is established in the region of interest, such as with the origin of the Cartesian coordinate system positioned in the lesion region included in the region of interest. In some embodiments, establishing the Cartesian coordinate system includes selecting a rotation axis as the Y-axis, randomly selecting a direction orthogonal to the Y-axis as the X-axis, and selecting a direction orthogonal to both the X-axis and the Y-axis as the Z-axis. In various embodiments, establishing the Cartesian coordinate system includes calculating a covariance matrix for every coordinate points in the lesion region and/or the region of interest. In some embodiments, establishing the Cartesian coordinate system further includes calculating an eigenvector and a corresponding eigenvalue for each covariance matrix. For example, the eigenvector corresponding with the largest eigenvalue is used as the central axis of the lesion region, which is used as the Y-axis according to some embodiments. The X-axis is then selected randomly by selecting a direction orthogonal to the Y-axis as the X-axis. The Z-axis is then selected by selecting a direction orthogonal to both the X-axis and the Y-axis as the Z-axis.

In various embodiments, the method S200 includes a process S210 of performing a maximum intensity projection on the region of interest along the Z-axis direction to obtain a planar image of a plurality of planar images. In certain examples, the process S210 is performed at a first (or initial) position (or orientation), such as a first relative position between the region of interest (e.g., selected in the process S206) and the coordinate system (e.g., established in the process S208). In various examples, the planar image obtained by performing the maximum intensity projection at the first position is used as the first planar image of the plurality of planar images. In certain examples, performing the maximum intensity projection generates a maximum intensity projection based on at least the maximum intensity pixel encountered on each ray (e.g., projection line) going through a target region (e.g., the region of interest). For example, performing the maximum intensity projection includes passing light rays through the region of interest and retaining the pixels with the highest intensity along each light ray within the region of interest, which collectively, the pixels are projected onto a two-dimensional plane to form a maximum intensity projection image of the region of interest.

In various embodiments, the method S200 includes a process S212 of rotating the Z-axis from the first direction to a second direction by a predetermined angle in a predetermined direction (e.g., clockwise or counterclockwise), performing the maximum intensity projection on the region of interest along the Z-axis in the second direction (e.g., a predetermined angle away from the first direction) to obtain a second planar image of the plurality of planar images, and repeating at least rotating the Z-axis by the predetermined angle in the predetermined direction and performing the maximum intensity projection on the region of interest along the Z-axis to obtain another planar image of the plurality of planar images after each rotation until the Z-axis is rotated back to the first direction (e.g., in the first position). In some embodiments, the process S212 includes repeatedly rotating the region of interest (e.g., instead of rotating the Z-axis and/or the coordinate system) in a preset direction by a preset angle from a first position, projecting the maximum intensity projection along the Z-axis direction after each rotation of the region of interest to obtain one of the plurality of planar images, until the region of interest is rotated back to a first position, where the first planar image is obtained.

In various embodiments, obtaining a planar image (e.g., of the plurality of planar images) includes rotating the region of interest in a first preset direction by a first preset angle about the Y-axis, performing the maximum intensity projection on the region of interest along the Z-axis direction to obtain a maximum intensity projection image to be used as a planar image of the plurality of planar images, rotating the region of interest in a preset direction (e.g., the same as the first direction) by a second preset angle (e.g., the same as the first preset angle) about the X-axis, performing the maximum intensity projection on the region of interest along the Z-axis direction to obtain a another maximum intensity projection image to be used as another planar image of the plurality of planar images, alternatively repeating the rotating about the Y-axis and the rotating about the X-axis until the region of interest is rotated back to the first position. In various examples, each rotation about the Y-axis and about the X-axis is followed by performing the maximum intensity projection on the region of interest along the Z-axis direction to obtain one maximum intensity projection image to be used as one of the plurality of planar images, except for the rotation back to the first position, which is not followed by performing the maximum intensity projection. In certain examples, the first preset direction and the second present direction is the same or different and is clockwise or counterclockwise. In some examples, the first preset angle and the second preset angle is the same or different and, according to some embodiments, is a quotient of 360° divided by a positive integer.

In various embodiments, the method S200 includes a process S214 of generating an animated display (or animated image) by grouping the plurality of planar images based on at least a predetermined order. In some examples, the process S214 includes generating the animated display by grouping the plurality of planar images based on at least an order identical to the sequence in which the plurality of planar images is obtained or based on at least an order reverse to the sequence in which the plurality of planar images is obtained. In certain embodiments, generating the animated display includes inputting the plurality of planar images into a video encoder to be processed (e.g., compressed) into a video format (e.g., MPEG4, H.264) or into an interchange file format (e.g., GIF).

In various embodiments, the process S214 of displaying the animated display related to the region of interest including the lesion region includes displaying the animated display via a display interface, such as a display interface of a CT system. In certain examples, displaying the animated display includes displaying a plurality of animated displays in a plurality of display windows (e.g., cells) in a display interface (e.g., a monitor, a screen). For example, the process S214 includes displaying each of the display of animated displays in one of the plurality of display windows. In some examples, displaying the animated display includes displaying a reconstructed image (e.g., a three-dimensional, multi-planar, and/or multi-surface image) including one or more reconstructed surfaces (e.g., curved surfaces) of a feature, an object, and/or a structure (e.g., a rib) in region of interest. In certain embodiments, displaying the animated display includes displaying one or more planar (e.g., two-dimensional) images corresponding to the reconstructed image (e.g., three-dimensional). For example, one or more planar images includes at least one cross-sectional image of the feature, object, or structure in the region of interest which. In some examples, at least one of the plurality of display windows is a floating window configured to display an animated display. In various examples, at least some display windows of the plurality of display windows are linked, such that when one of the linked display window is manipulated, the rest of the linked display windows are modified in response to the manipulation.

In certain examples, the process S214 of displaying the animated display includes receiving user input (e.g., from a physician), such as dynamically (e.g., in real-time) receiving user input and displaying one or more adjusted animated display in response to the user input. For example, displaying one or more adjusted animated displays includes generating the one or more adjusted animated displays based on at least performing one or more of processes S202, S204, S206, S208, S210, and S212 based on at least the received user input. In certain examples, receiving user input includes receiving one or more preferences and/or settings (e.g., viewing habits, threshold values, default values, target values), which, in some examples, helps improve diagnostic efficiency and/or accuracy. In various examples, receiving user input includes receiving a display speed, a forward, rewind, speed up, slow down, loop, and/or pause instruction, which is applied to the animated display.

In some embodiments, a method for displaying a medical image includes acquiring an original image, obtaining a lesion region in the original image, selecting a region of interest based on at least the lesion region, establishing a Cartesian coordinate system including an X-axis, a Y-axis, and a Z-axis, performing a maximum intensity projection on the region of interest along the Z-axis in a first direction to obtain a first planar image of the plurality of planar images, rotating the Z-axis from the first direction to a second direction by a predetermined angle in a predetermined direction, performing the maximum intensity projection on the region of interest along the Z-axis in the second direction to obtain a second planar image of the plurality of planar images, and repeating at least rotating the Z-axis by the predetermined angle in the predetermined direction and performing the maximum intensity projection on the region of interest along the Z-axis to obtain another planar image of the plurality of planar images until the Z-axis is rotated back to the first direction, generating an animated display by grouping the plurality of planar images based on at least a predetermined order, and displaying the animated display related to the region of interest including the lesion region.

In certain embodiments, a method for displaying a medical image includes acquiring the original image, selecting a lesion region in the original image, selecting a region of interest, based on the lesion region, establishing a Cartesian coordinate system, performing the maximum intensity projection at an initial position along the Z-axis direction to obtain a maximum intensity projection as a first planar image of a plurality of planar images, repeatedly rotating the region of interest in a preset direction by a preset angle until the region of interest is rotated back to the initial position, performing the maximum intensity projection along the Z-axis following each rotation of the region of interest to obtain another maximum intensity projection as another planar image of the plurality of planar images, generating an animated display (or image) by grouping the plurality of planar images based on at least a predetermined order, and displaying the animated display related to the region of interest including the lesion region. In various examples, the animated display helps a physician to more efficiently, effectively, and/or clearly observe a lesion region.

Figure 3:
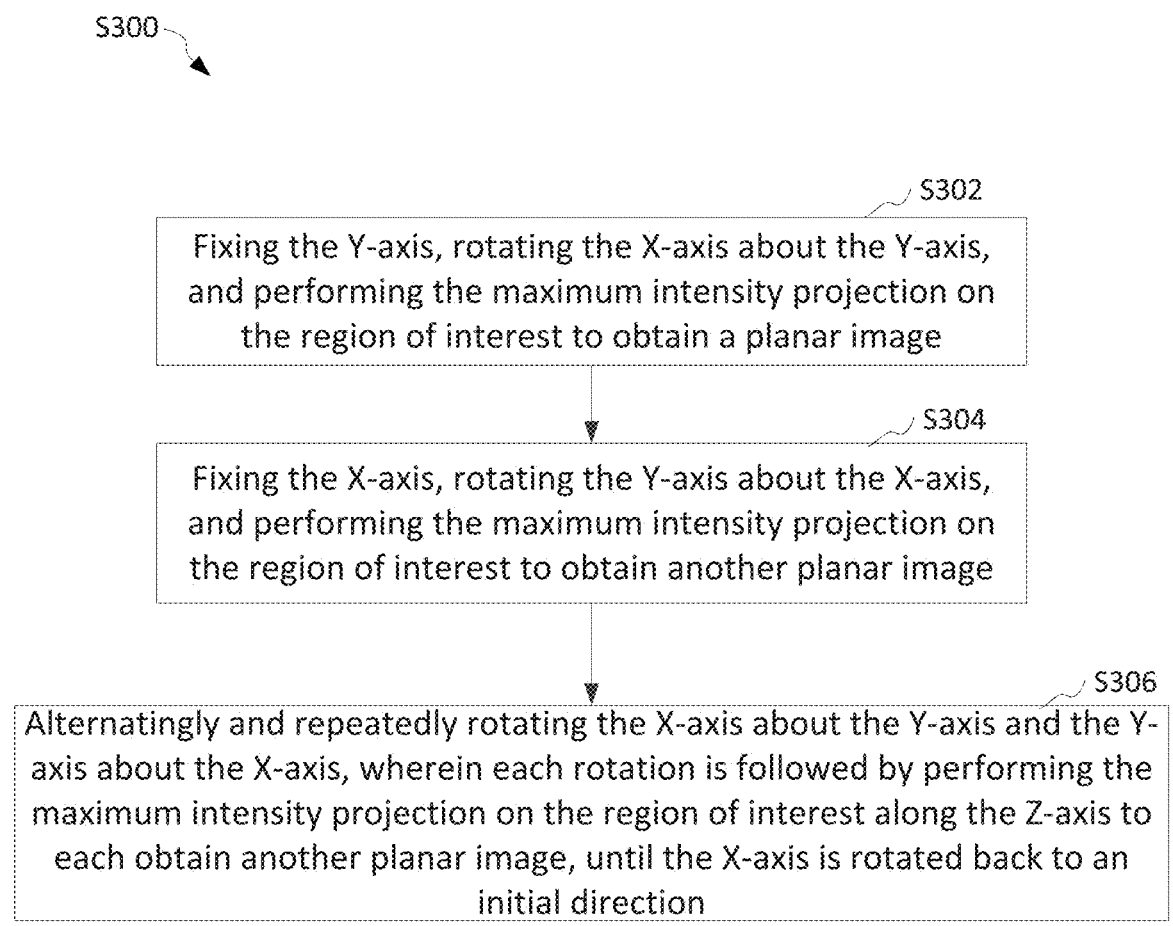
FIG. 3 is a simplified diagram showing a process for obtaining a planar image, according to some embodiments of the present invention.

FIG. 3 is a simplified diagram showing a process S300 for obtaining a planar image, according to some embodiments of the present invention. This diagram is merely an example, which should not unduly limit the scope of the claims. One of ordinary skill in the art would recognize many variations, alternatives, and modifications. In various embodiments, the process S300 includes a process S302 of fixing the Y-axis, rotating the X-axis about the Y-axis (e.g., in a first predetermined direction by a first predetermined angle), and performing a maximum intensity projection on the region of interest along the Z-axis to obtain a planar image (e.g., of a plurality of planar images), a process S304 of fixing the X-axis, rotating the Y-axis about the X-axis (e.g., in a second predetermined direction by a second predetermined angle), and performing a maximum intensity projection on the region of interest along the Z-axis to obtain another planar image (e.g., of the plurality of planar images), and/or a process S306 of alternatingly and repeatedly rotating the X-axis about the Y-axis and the Y-axis about the X-axis (or only one of rotating the X-axis about the Y-axis or rotating the Y-axis about the X-axis), wherein each rotation is followed by performing the maximum intensity projection on the region of interest along the Z-axis to each obtain another planar image (e.g., of the plurality of images), until the X-axis is rotated back to an initial direction. In some examples, only one of process S302 and process S304 is performed. In certain examples, the first predetermined direction and/or the second predetermined direction is clockwise or counterclockwise. In some examples, the first and/or the second predetermined angle is small (e.g., 1° or 0.5°). In certain embodiments, the first predetermined angle is the same as the second predetermined angle. Although the above has been shown using a selected group of (sub) processes (steps) for the process, there can be many alternatives, modifications, and variations. For example, some of the processes may be expanded and/or combined. Other processes may be inserted to those noted above. Depending upon the embodiment, the sequence of processes may be interchanged with others replaced.

In certain embodiments, the process S300 includes fixing the coordinate system, rotating the region of interest about the Y-axis (e.g., in a first predetermined direction by a first predetermined angle), and performing a maximum intensity projection on the region of interest along the Z-axis to obtain a planar image (e.g., of a plurality of images). In some embodiments, the process S300 includes fixing the coordinate system, rotating the region of interest about the X-axis (e.g., in a second predetermined direction by a second predetermined angle), and performing a maximum intensity projection on the region of interest along the Z-axis to obtain another planar image (e.g., of the plurality of planar images). In some examples, only one of rotating about the Y-axis and rotating about the X-axis is performed. In certain embodiments, the process S300 includes alternatingly and repeatedly rotating the region of interest about the Y-axis and/or about the X-axis, wherein each rotation is followed by performing the maximum intensity projection on the region of interest along the Z-axis to each obtain another planar image (e.g., of the plurality of images), until the region of interest is rotated back to an initial direction. In some examples, the first predetermined direction and/or the second predetermined direction is clockwise or counterclockwise. In various examples, the first predetermined direction is the same or different (e.g., reversed) with the second predetermined direction. In some examples, the first and/or the second predetermined angle is small (e.g., 1° or 0.5°). In certain embodiments, the first predetermined angle is the same as the second predetermined angle.

In some examples, the method S300 for acquiring a planar image can obtain an accurate planar image showing a lesion region, and then using the acquired planar image to generate an animated (e.g., dynamic) display (e.g., image or video), which, in some examples, help makes the lesion region more informative and/or clear to enable a physician to more accurately observe the lesion region, saving the physician valuable time in diagnosing a lesion.

It should be understood that although the various processes in the flowcharts of FIGS. 1-3 are sequentially displayed as indicated by the arrows, these processes are not necessarily performed in the order indicated by the arrows. The execution of these steps is not strictly limited, and the processes may be performed in other orders. Moreover, at least some of the processes in FIGS. 1-3 may include a plurality of sub-processes or stages, which are not necessarily performed at the same time, but may be executed at different times. The order of execution of these sub-processes or stages is not necessarily sequential but may be performed alternatingly.

Figure 4:
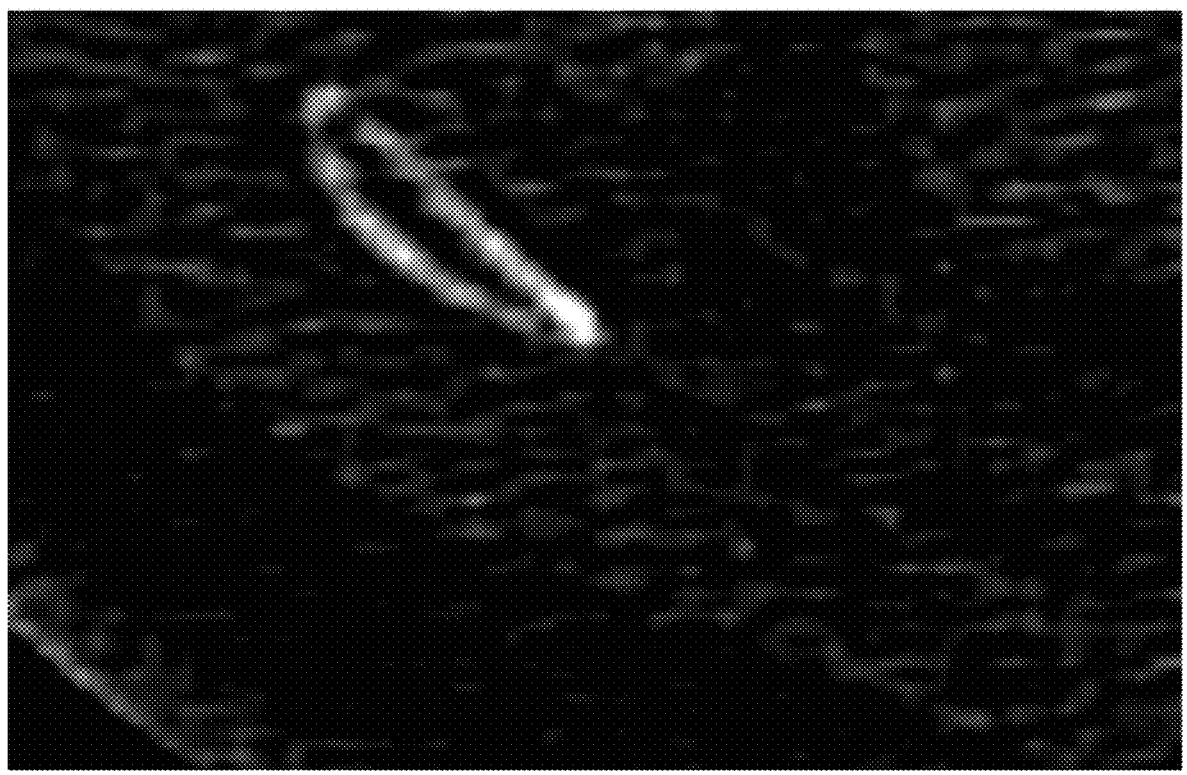
FIG. 4 shows an animated display including a rib fracture at a first viewing state, according to some embodiments of the present invention.
Figure 5:
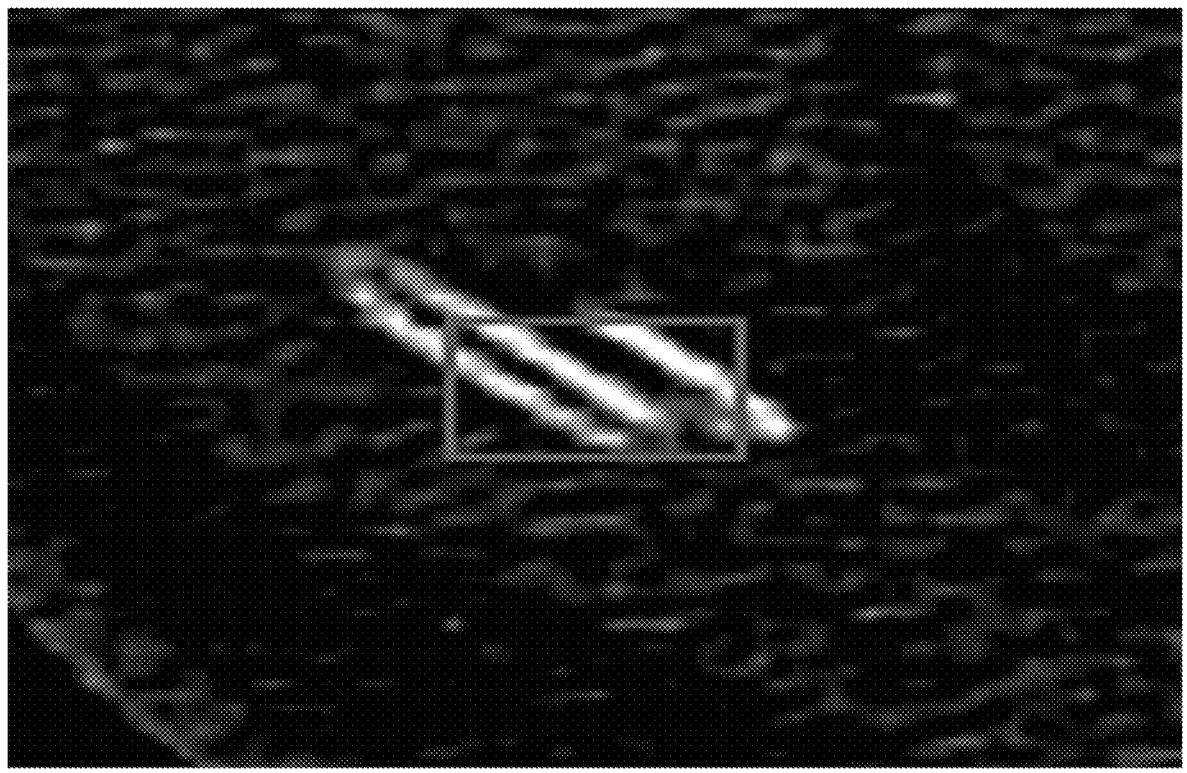
FIG. 5 shows the animated display of FIG. 4 at a second viewing state, according to some embodiments of the present invention.
Figure 6:
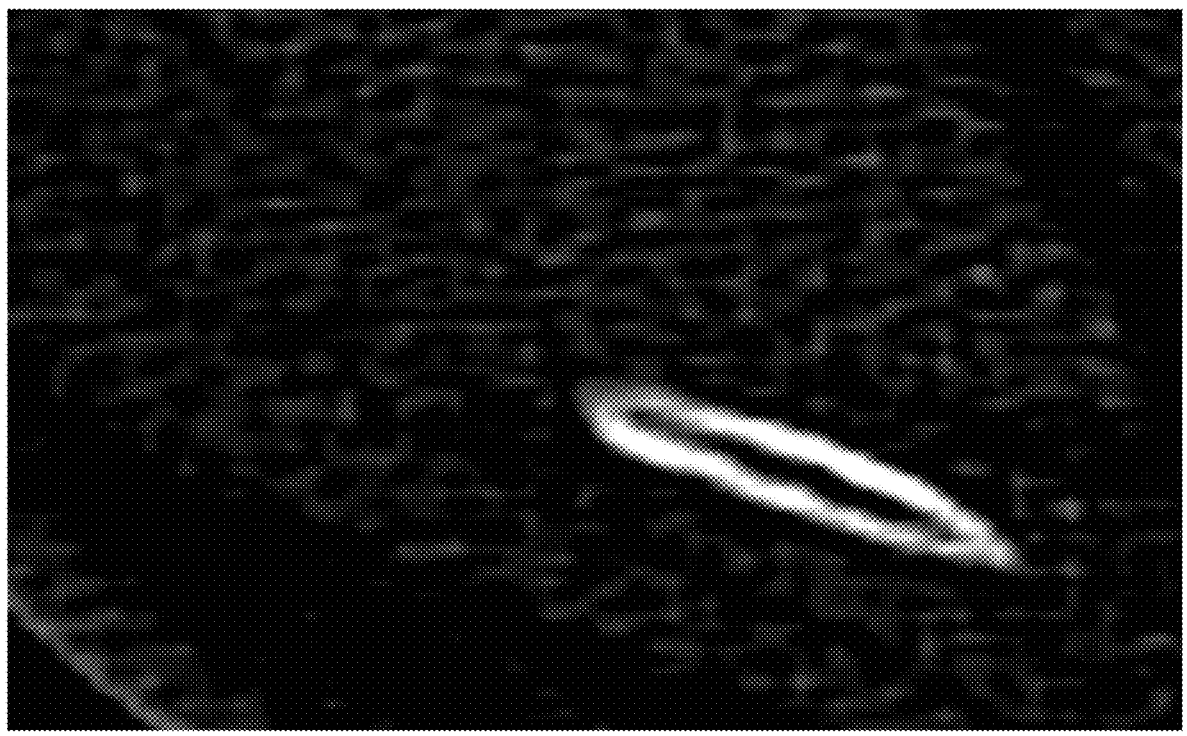
FIG. 6 shows the animated display of FIG. 4 at a third viewing state, according to some embodiments of the present invention.

FIGS. 4-6 show an animated display including a rib fracture (a lesion) at a first viewing state, a second viewing state, and a third viewing state, respectively, according to some embodiments of the present invention. For example, the first state, the second state, and the third state each corresponds to a different moment (e.g., chronologically selected) of the displaying (e.g., process S112 or process S214) of the animated display. In certain embodiments, displaying the animated display includes displaying a bounding box labeling the region of interest and/or the lesion region (e.g., the rib fracture, as shown in FIG. 5).

Figure 7:
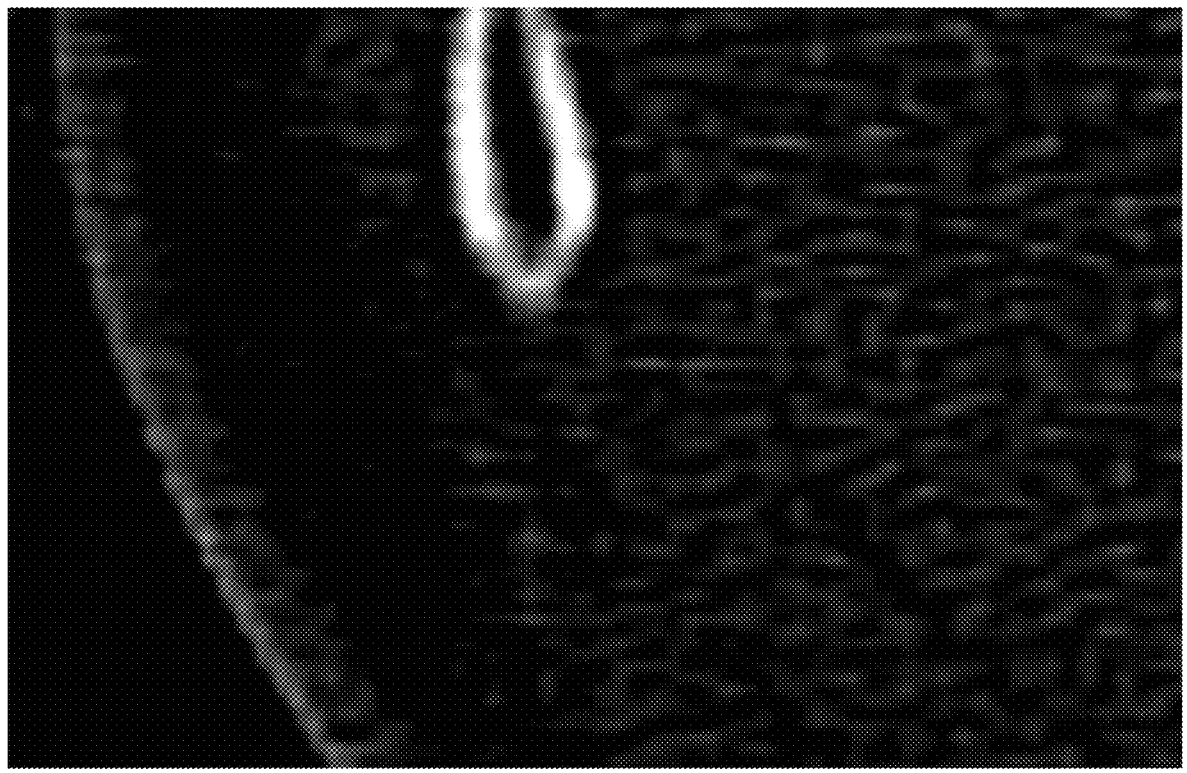
FIG. 7 shows an animated display including another rib fracture at a first viewing state, according to some embodiments of the present invention.
Figure 8:
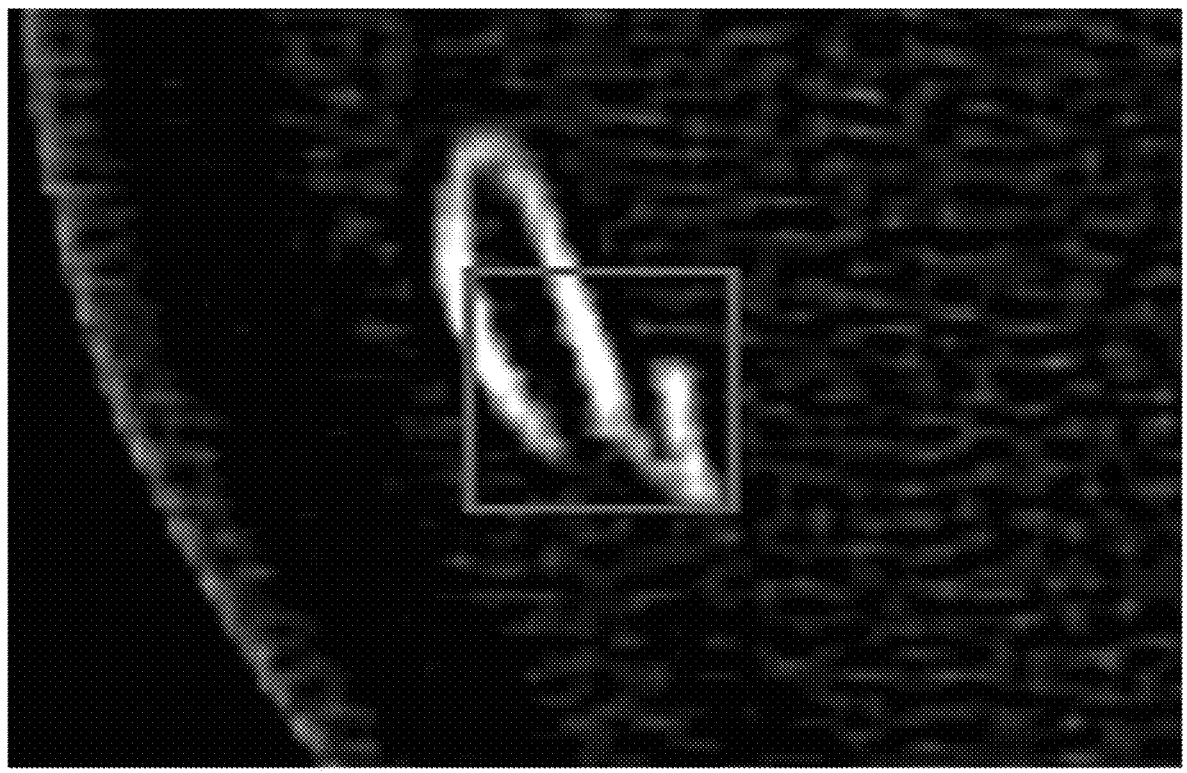
FIG. 8 shows the animated display of FIG. 7 at a second viewing state, according to some embodiments of the present invention.
Figure 9:
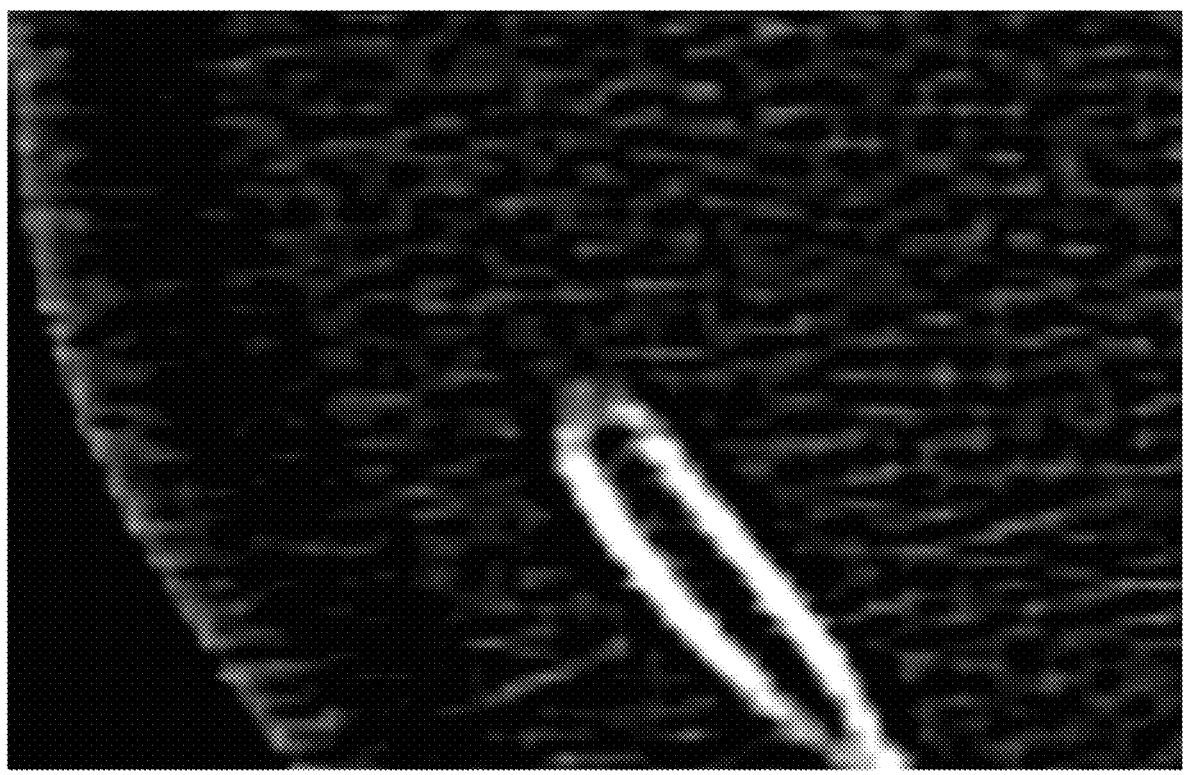
FIG. 9 shows the animated display of FIG. 7 at a third viewing state, according to some embodiments of the present invention.

FIGS. 7-9 show another animated display including a rib fracture (a lesion) at a first viewing state, a second viewing state, and a third viewing state, respectively, according to some embodiments of the present invention. For example, the first state, the second state, and the third state each corresponds to a different moment (e.g., chronologically selected) of the displaying (e.g., process S112 or process S214) of the animated display. In certain embodiments, displaying the animated display includes displaying a bounding box labeling the region of interest and/or the lesion region (e.g., the rib fracture, as shown in FIG. 8).

Figure 10:
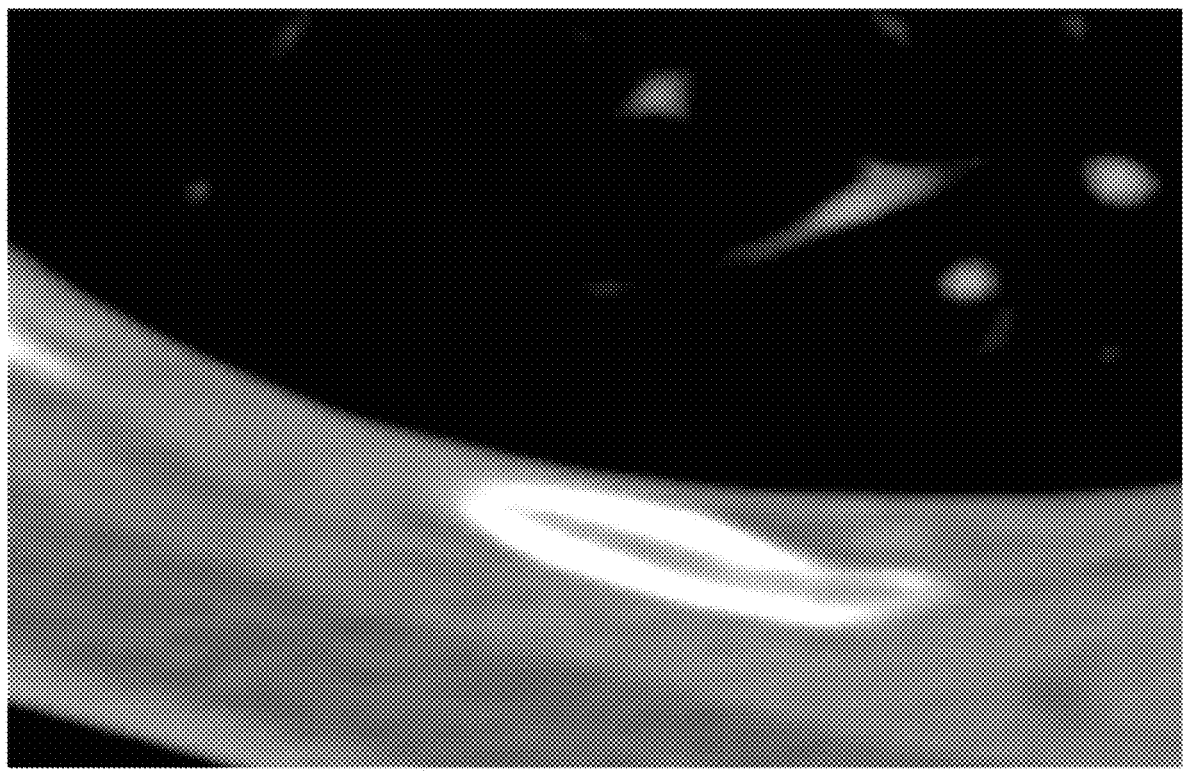
FIG. 10 shows an animated display including a pulmonary nodule at a first viewing state, according to some embodiments of the present invention.
Figure 11:
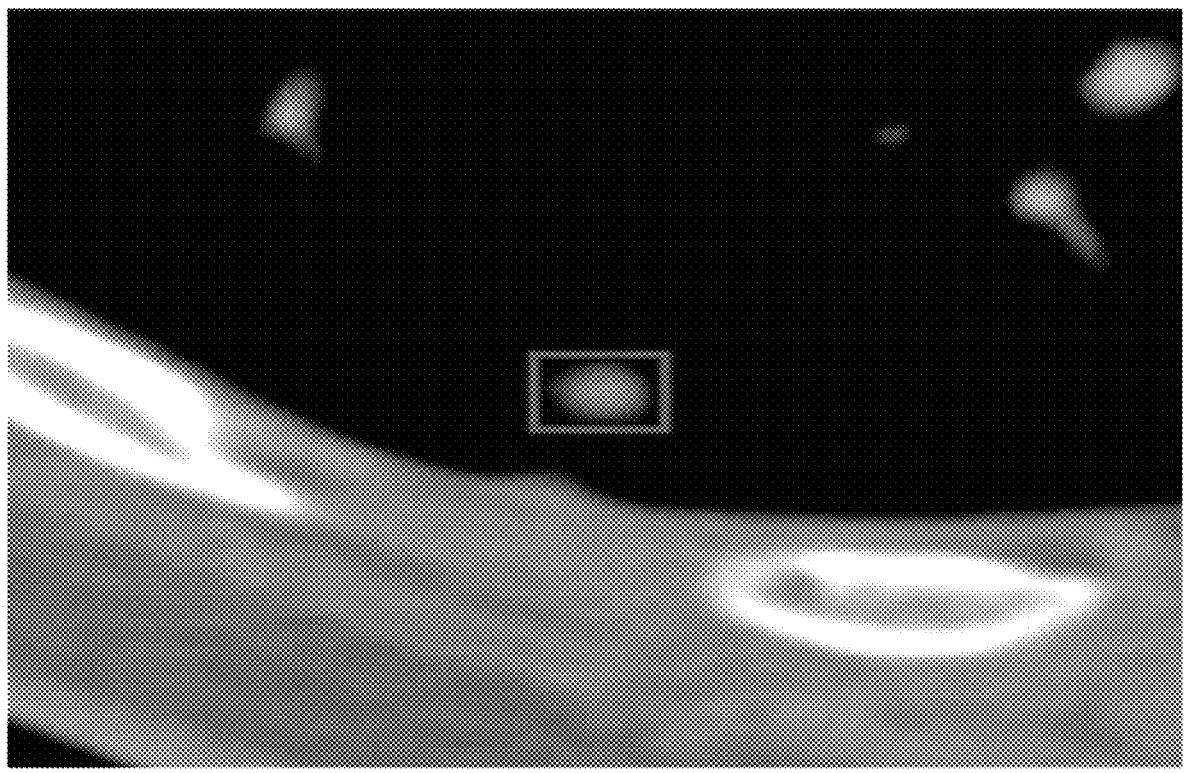
FIG. 11 shows the animated display of FIG. 10 at a second viewing state, according to some embodiments of the present invention.
Figure 12:
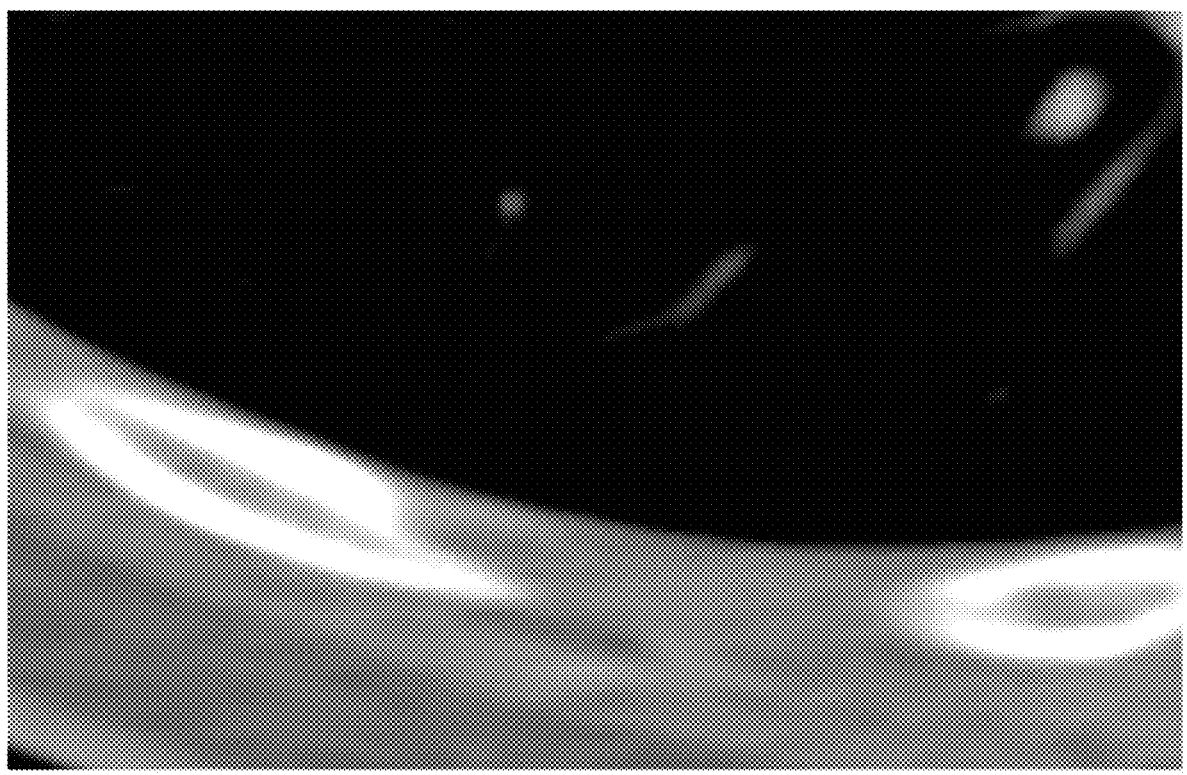
FIG. 12 shows the animated display of FIG. 10 at a third viewing state, according to some embodiments of the present invention.

FIGS. 10-12 show an animated display including a pulmonary nodule (a lesion) at a first viewing state, a second viewing state, and a third viewing state, respectively, according to some embodiments of the present invention. For example, the first state, the second state, and the third state each corresponds to a different moment (e.g., chronologically selected) of the displaying (e.g., process S112 or process S214) of the animated display. In certain embodiments, displaying the animated display includes displaying a bounding box labeling the region of interest and/or the lesion region (e.g., a nodule region, as shown in FIG. 11).

Figure 13:
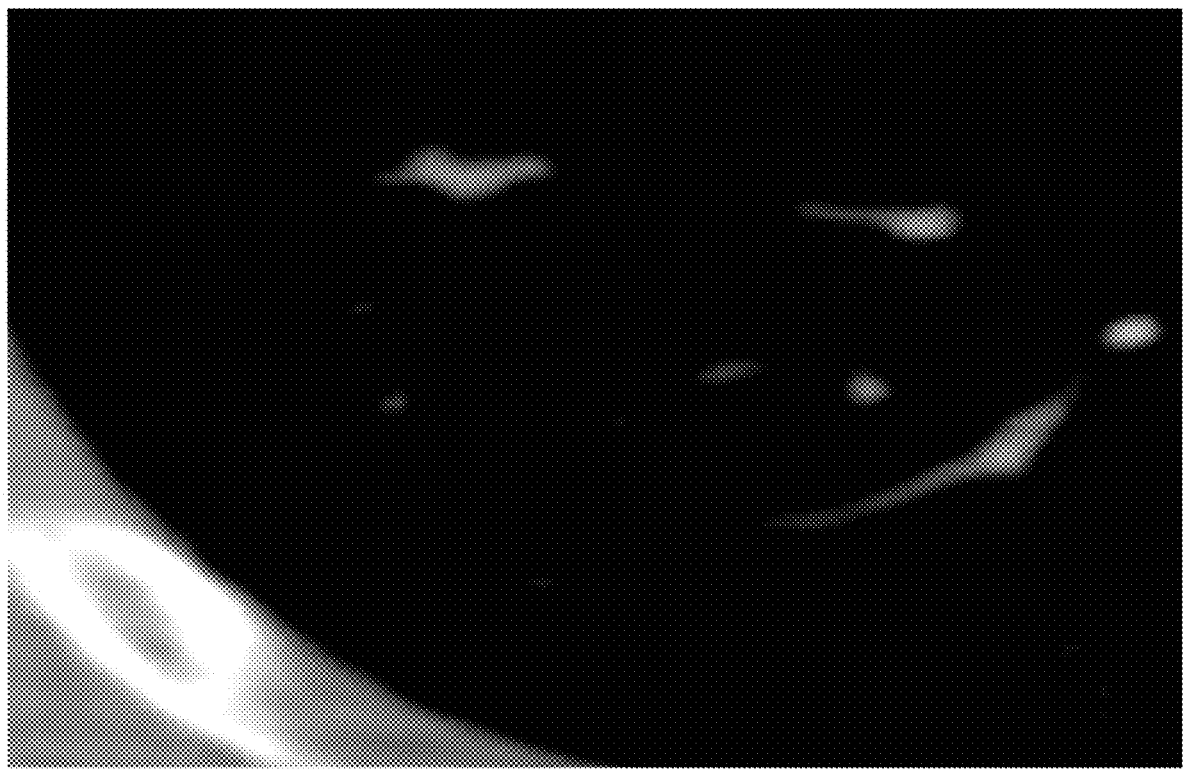
FIG. 13 shows an animated display including another pulmonary nodule at a first viewing state, according to some embodiments of the present invention.
Figure 14:
FIG. 14 shows the animated display of FIG. 13 at a second viewing state, according to some embodiments of the present invention.
Figure 15:
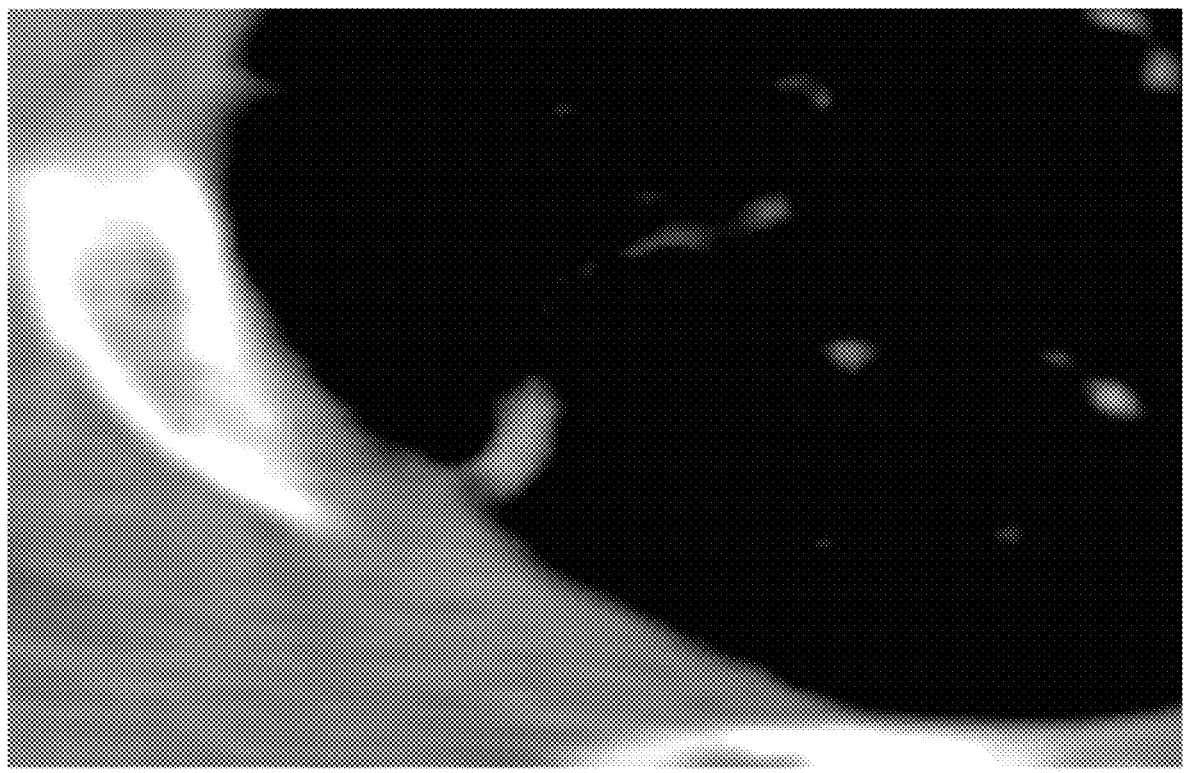
FIG. 15 shows the animated display of FIG. 13 at a third viewing state, according to some embodiments of the present invention.

FIGS. 13-15 show another animated display including a pulmonary nodule (a lesion) at a first viewing state, a second viewing state, and a third viewing state, respectively, according to some embodiments of the present invention. For example, the first state, the second state, and the third state each corresponds to a different moment (e.g., chronologically selected) of the displaying (e.g., process S112 or process S214) of the animated display. In certain embodiments, displaying the animated display includes displaying a bounding box labeling the region of interest and/or the lesion region (e.g., a nodule region, as shown in FIG. 14).

Figure 16:
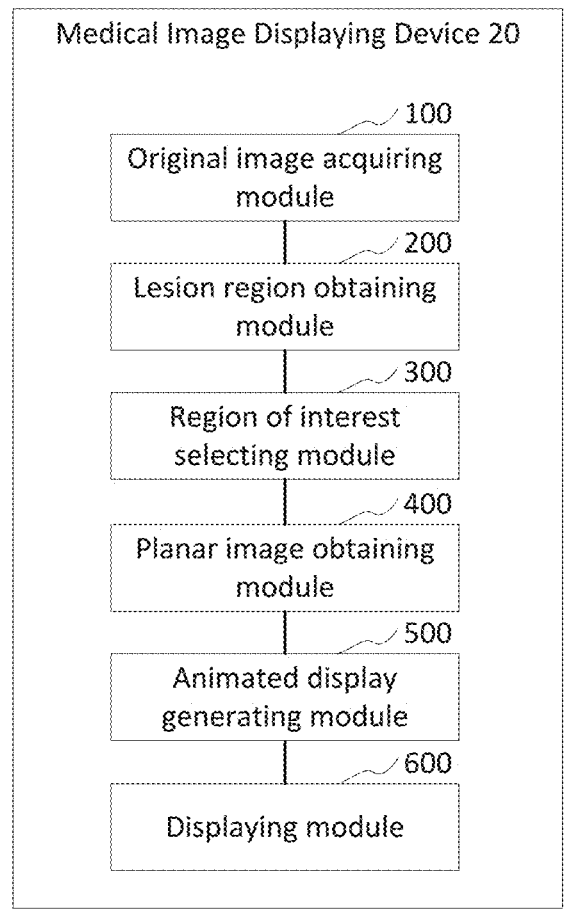
FIG. 16 is a simplified diagram showing a system for displaying a medical image, according to some embodiments of the present invention.

FIG. 16 is a simplified diagram showing a system 20 for displaying a medical image, according to some embodiments of the present invention. This diagram is merely an example, which should not unduly limit the scope of the claims. One of ordinary skill in the art would recognize many variations, alternatives, and modifications. In some examples, the system 20 includes an original image acquiring module 100, a lesion region obtaining module 200, a region of interest selecting module 300, a planar image obtaining module 400, an animated display generating module 500, and/or a displaying module 600. In certain examples, the original image acquiring module 100 is configured to perform the process S102, the lesion region obtaining module 200 is configured to perform the process S104, the region of interest selecting module 300 is configured to perform the process S106, the planar image obtaining module 400 for performing the process S108, the animated display generating module 500 is configured to perform the process S110, and/or the displaying module 600 is configured to perform the process S112. Although the above has been shown using a selected group of components for the system, there can be many alternatives, modifications, and variations. For example, some of the components may be expanded and/or combined. Other components may be inserted to those noted above. Depending upon the embodiment, the arrangement of components may be interchanged with others replaced.

In certain embodiments, the original image acquiring module 100 is configured to acquire an original image (e.g., of a target), the lesion region obtaining module 200 is configured to obtain a lesion region in the original image, the region of interest selecting module 300 is configured to select a region of interest in the original image based on at least the lesion region (e.g., the region of interest includes the lesion region), the planar image obtaining module 400 is configured to obtain a plurality of planar images of the region of interest from the original image (e.g., of the target) based on at least a predetermined setting (e.g., acquisition setting), the animated display generating module 500 is configured to generate an animated display by grouping the plurality of planar images based on at least a predetermined order, and/or the displaying module is configured to display the animated display (e.g., in a predetermined displaying setting) related to the region of interest and/or the lesion region. In certain embodiments, the original image acquiring module 100 is configured to input the original image into a neural network trained based on a set of training images to obtain the lesion region. In some embodiments, the animated display generating module 500 is configured to generate an animated display by grouping the plurality of planar images in the order (e.g., an acquisition order) in which the plurality of planar images is obtained or in the reverse order in which the plurality of planar images is obtained.

Figure 17:
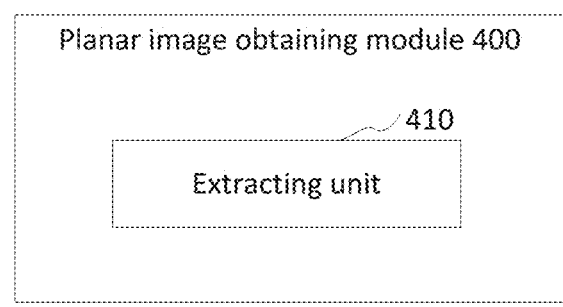
FIG. 17 is a simplified diagram showing a planar image obtaining module, according to some embodiments of the present invention.

FIG. 17 is a simplified diagram showing a planar image obtaining module 400, according to some embodiments of the present invention. This diagram is merely an example, which should not unduly limit the scope of the claims. One of ordinary skill in the art would recognize many variations, alternatives, and modifications. In some examples, the planar image obtaining module 400 includes an extracting unit 410 configured to sequentially obtain the plurality of planar images along a predetermined direction, wherein the plurality of planar images is perpendicular to the predetermined direction. Although the above has been shown using a selected component for the system (module), there can be many alternatives, modifications, and variations. For example, some of the components may be expanded and/or combined. Other components may be inserted to those noted above. Depending upon the embodiment, the arrangement of components may be interchanged with others replaced.

Figure 18:
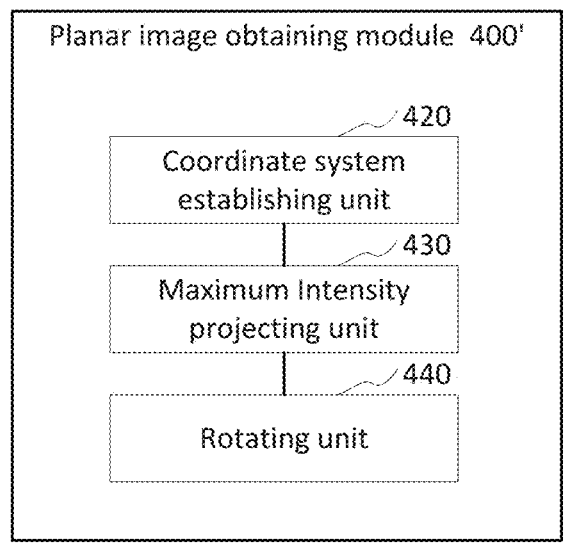
FIG. 18 is a simplified diagram showing another planar image obtaining module, according to some embodiments of the present invention.

FIG. 18 is a simplified diagram showing another planar image obtaining module 400', according to some embodiments of the present invention. This diagram is merely an example, which should not unduly limit the scope of the claims. One of ordinary skill in the art would recognize many variations, alternatives, and modifications. In various examples, the planar image obtaining module 400' includes a coordinate system establishing unit 420, a maximum intensity projecting unit 430, and/or a rotating unit 440. Although the above has been shown using a selected group of components for the module, there can be many alternatives, modifications, and variations. For example, some of the components may be expanded and/or combined. Other components may be inserted to those noted above. Depending upon the embodiment, the arrangement of components may be interchanged with others replaced.

In certain embodiments, the coordinate system establishing unit 420 is configured to establish a Cartesian (e.g., three-dimensional) coordinate system (e.g., including an X-axis, a Y-axis, and a Z-axis). In some examples, the coordinate system is established in the region of interest and/or the lesion region of the original image. For example, the origin of the coordinate system is in the region of interest and/or the lesion region of the original image. For example, the origin of the coordinate system is in the origin of the region of interest of interest and/or of the lesion region of the original image. In various embodiments, the maximum intensity projecting unit 430 is configured to perform the maximum intensity projection on the region of interest and/or the lesion region along the Z-axis direction to obtain a maximum intensity projection image to be used as a planar image (e.g., of a plurality of planar images). In various embodiments, the rotating unit 440 is configured to rotate the Z-axis, the coordinate system, or the region of interest in a predetermined direction in a predetermined angle. In some examples, the maximum intensity projection unit 430 is configured to perform the maximum intensity projection when the Z-axis, the coordinate system, or the region of interest is in a first position. In certain examples, the maximum intensity projection unit 430 is configured to perform the maximum intensity projection following each rotating of the Z-axis, the coordinate system, or the region of interest, until the rotation returns the rotated (e.g., the Z-axis, the coordinate system, or the region of interest) back to the first position (see rotating unit 440).

Figure 19:
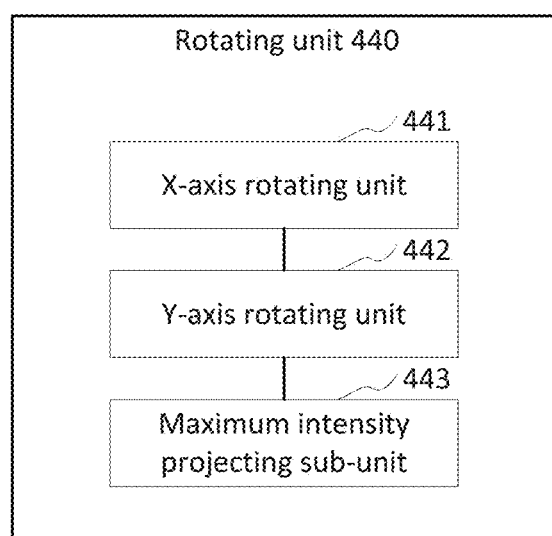
FIG. 19 is a simplified diagram showing a rotating unit, according to some embodiments of the present invention.

FIG. 19 is a simplified diagram showing a rotating unit 440, according to some embodiments of the present invention. This diagram is merely an example, which should not unduly limit the scope of the claims. One of ordinary skill in the art would recognize many variations, alternatives, and modifications. In some examples, the rotating unit 440 includes an X-axis rotating unit 441, a Y-axis rotating unit 442, and/or a maximum intensity projecting sub-unit 443. Although the above has been shown using a selected group of components for the unit, there can be many alternatives, modifications, and variations. For example, some of the components may be expanded and/or combined. Other components may be inserted to those noted above. Depending upon the embodiment, the arrangement of components may be interchanged with others replaced.

In various examples, the X-axis rotating unit 441 is configured to rotate the Z-axis, the coordinate system, or the region of interest, about the X-axis, such as in a predetermined direction (e.g., clockwise or counterclockwise) by a predetermined angle, such as from a first position. In various examples, the Y-axis rotating unit 442 is configured to rotate the Z-axis, the coordinate system, or the region of interest, about the Y-axis, such as in a predetermined direction (e.g., clockwise or counterclockwise) by a predetermined angle. In some examples, the X-axis rotating unit 441 and the Y-axis rotating unit 442 rotate the Z-axis, the coordinate system, or the region of interest alternatingly about the X-axis and the Y-axis, respectively. In various embodiments, the maximum intensity projecting sub-unit 443 is configured to perform the maximum intensity projection following each rotating of the Z-axis, the coordinate system, or the region of interest, until the rotation returns the rotated (the Z-axis, the coordinate system, or the region of interest) back to the first position. In certain examples, rotating the Z-axis is performed while maintaining the orthogonal relationships of the Cartesian coordinate system (e.g., between the X-axis, the Y-axis, and the Z-axis).

Figure 20:
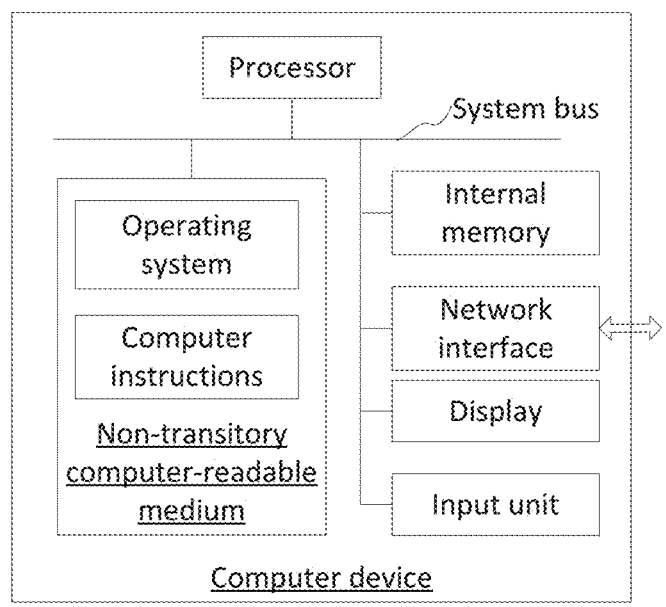
FIG. 20 is a simplified diagram showing a computer device for displaying a medical image, according to some embodiments of the present invention.

FIG. 20 is a simplified diagram showing a computer device for displaying a medical image, according to some embodiments of the present invention. This diagram is merely an example, which should not unduly limit the scope of the claims. One of ordinary skill in the art would recognize many variations, alternatives, and modifications. In various examples, the computer device includes a processor, a memory, a network interface, a display, an input unit, and/or a system bus. Although the above has been shown using a selected group of components for the device, there can be many alternatives, modifications, and variations. For example, some of the components may be expanded and/or combined. Other components may be inserted to those noted above. Depending upon the embodiment, the arrangement of components may be interchanged with others replaced. In some examples, the computer device is a terminal.

In various examples, the computer device includes a processor, a memory, a network interface, a display (e.g., screen), and an input unit all connected by a system bus. In certain examples, the processor is configured to provide computing and/or control capabilities. In certain embodiments, the memory includes a non-transitory computer-readable medium and an internal memory. In various examples, the non-transitory computer-readable medium is configured to store an operating system and computer instructions (e.g., as a program). In certain embodiments, the internal memory provides a working environment for the operating system and the computer instructions. In various embodiments, the network interface is configured to communicate with an external terminal via a network connection. In various examples, the computer instructions are executable by the processor, such as to implement a method for displaying a medical image (e.g., as described in FIG. 1 and/or FIG. 2). In certain examples, the display includes a liquid crystal display or an electronic ink display. In some examples, the input unit includes a touch interface, a tracking unit (e.g., a trackball, a mouse, or a trackpad), and/or a keyboard. It is understood by those skilled in the art that the structures shown in FIG. 20 are only block diagrams of a part of the structure related to the solution of the present application and does not constitute a limitation of the computer device to which the solution of the present application is applied. The specific computer device may include more or fewer components than those shown in the figures, or some components may be combined or arranged differently.

In some examples, some or all processes (e.g., steps) of the method S100 and/or method S200 are performed by the computer device. In certain examples, some or all processes (e.g., steps) of the method S100 and/or method S200 are performed by a computer and/or a processor directed by a code. For example, a computer includes a server computer and/or a client computer (e.g., a smartphone). In some examples, some or all processes (e.g., steps) of the S100 and/or method S200 are performed according to instructions included by a non-transitory computer-readable medium (e.g., in a computer program product, such as a mobile app and/or a web app). For example, a non-transitory computer-readable medium is readable by a computer including a server computer and/or a client computer (e.g., a smartphone). As an example, instructions included by a non-transitory computer-readable medium are executed by a processor including a processor of a server computer and/or a processor of a client computer (e.g., a smartphone).

In some examples, a computer device includes a memory and a processor, the memory storing a computer program, wherein the processor executes the computer program to implement the processes including: acquiring an original image of a target; obtaining a lesion region in the original image; selecting a region of interest in the original image based on at least the lesion region, the region of interest including the lesion region; obtaining a plurality of planar images of the region of interest from the original image of the target based on at least a predetermined setting; generating an animated display by grouping the plurality of planar images based on at least a predetermined order; and displaying the animated display related to the region of interest including the lesion region.

In some embodiments, an animated display method of automatically detection lesion candidates by a computer aided diagnosis (CAD) technology is disclosed. Firstly, the CAD algorithm, for instance, deep learning based neural network, is performed or run to obtain the positions and scales of all lesion candidates in one or more 3D images. Secondly, for each lesion candidate, cropping a region of interest from the 3D image which centers on the lesion and encompasses the whole lesion with sufficient context in the background. Thirdly, grouping all the slices (e.g., from cropping the region of interest) to generate a video clip or animated gif which can be played or displayed, such as automatically (e.g., at the CAD software user interface) to a user (e.g., a radiologist) for viewing and learning the contextual information of the lesion candidate and make further decision whether to accept or reject the lesion candidate from a final diagnosis report. The user can choose any frame-rate to play the video clip, fast forward or rewind, pause or play in loop.

In some embodiments, planar slice images are automatically cropped from CT images of detected rib fractures and/or lung nodules to be displayed in animated fashion. The proposed animated visualization method can help radiologists to learn the appearance of the lesion and contextual information very quickly to make diagnosis decision without the need of manually sliding through slices. In certain examples, the generated video or gifs are displayed from transverse planes of the starting 3D CT volume, but can also be from any planes including but not limited to coronal planes or sagittal planes, or planes perpendicular to the medial axis of a structure of interest such as a rib.

Figure 21:
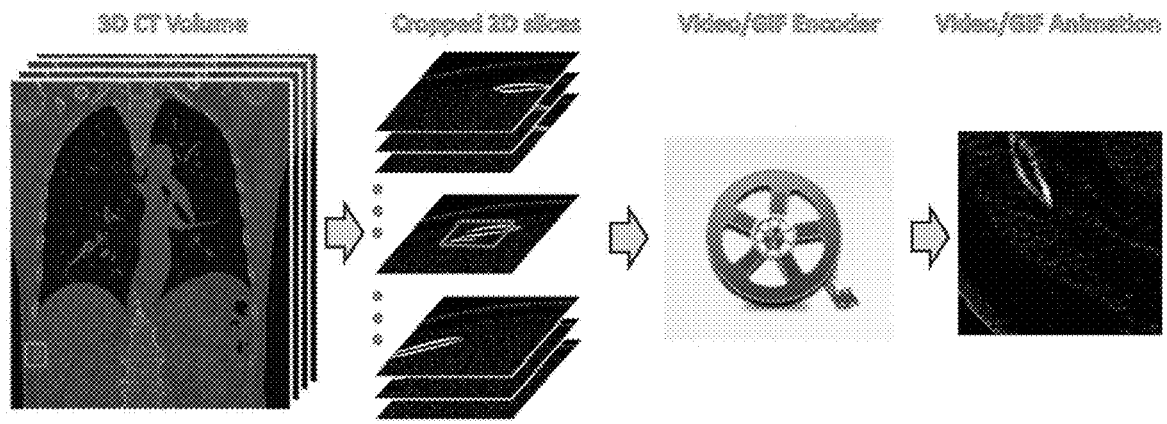
FIG. 21 is a simplified diagram showing a method for displaying a medical image based on coplanar slicing, according to some embodiments of the present invention.

FIG. 21 is a simplified diagram showing a method for displaying a medical image based on coplanar slicing, according to some embodiments of the present invention. The method includes cropping or slicing a number of sliced 2D images from axial planes centering on each detected lesion with scale proportional to the lesion size (e.g., true-to-scale). The cropped images encompass the whole detected lesion with sufficient context to help radiologists review detected lesions. Those 2D images are next sorted in descending or ascending order (e.g., of their z coordinates) and input into a MPEG-4 or H.264 video encoder to generate a video of the lesion or a GIF image that displays the lesion in a simplified animated fashion.

Figure 22:
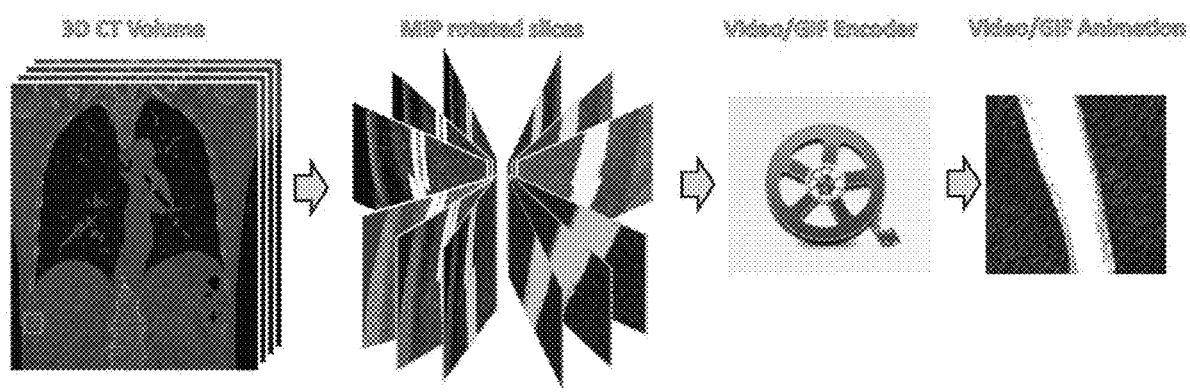
FIG. 22 is a simplified diagram showing a method for displaying a medical image based on maximum intensity projection, according to some embodiments of the present invention.

FIG. 22 is a simplified diagram showing a method for displaying a medical image based on maximum intensity projection, according to some embodiments of the present invention. The method includes choosing the center of a detected lesion as an origin and selecting a rotation axis as the Y-axis for the 2D images to be obtained. Next, randomly selecting an X-axis in the 3D space which is orthogonal to the Y-axis and using the cross product to obtain the Z-axis. The intensity of each pixel in a 2D frame is selected as the maximum intensity value of all voxels in the 3D CT volume passing through the pixel along the Z-axis within certain distance from the pixel. After obtaining the first 2D frame as a 2D image, X-axis is rotated around Y-axis (clockwise or counterclockwise) by a small angle, following by repeating the processes to obtain a second image from a second 2D frame. The whole procedure is repeated until the X-axis goes back to the original direction of the first frame. All frames are then fed into the MPEG-4 or H.264 video encoder to generate a video or a GIF file.

In various embodiments, a computer-implemented method for displaying a medical image includes acquiring an original image of a target; obtaining a lesion region in the original image; selecting a region of interest in the original image based on at least the lesion region, the region of interest including the lesion region; obtaining a plurality of planar images of the region of interest from the original image of the target based on at least a predetermined setting; generating an animated display by grouping the plurality of planar images based on at least a predetermined order; and displaying the animated display related to the region of interest including the lesion region. In some examples, the method is implemented according to at least the method S100 of FIG. 1. In certain examples, the method is implemented at least by the medical image displaying device 20 of FIG. 16.

In some embodiments, obtaining a lesion region in the original image includes obtaining the lesion region by inputting the original image into a neural network trained by a set of training images. In certain embodiments, obtaining a plurality of planar images of the region of interest from the original image of the target includes sequentially obtaining the plurality of planar images along a predetermined direction, the plurality of planar images being perpendicular to the predetermined direction.

In various examples, obtaining a plurality of planar images of the region of interest from the original image of the target includes establishing a Cartesian coordinate system including an X-axis, a Y-axis, and a Z-axis; performing a maximum intensity projection on the region of interest along the Z-axis in a first direction to obtain a first planar image of the plurality of planar images; rotating the Z-axis from the first direction to a second direction by a predetermined angle; and performing the maximum intensity projection on the region of interest along the Z-axis in the second direction to obtain a second planar image of the plurality of planar images.

In various examples, obtaining a plurality of planar images of the region of interest from the original image of the target further includes repeating at least rotating the Z-axis by the predetermined angle and performing the maximum intensity projection on the region of interest along the Z-axis to obtain another planar image of the plurality of planar images until the Z-axis is rotated back to the first direction.

In certain examples, repeating at least rotating the Z-axis by the predetermined angle and performing the maximum intensity projection on the region of interest along the Z-axis includes fixing the Y-axis, rotating the X-axis about the Y-axis, and performing the maximum intensity projection on the region of interest; and fixing the X-axis, rotating the Y-axis about the X-axis, and performing the maximum intensity projection on the region of interest. In some examples, rotating the Z-axis from the first direction to a second direction by a predetermined angle includes fixing the Y-axis and rotating the X-axis about the Y-axis from an initial direction in a predetermined direction. In certain embodiments, the predetermined direction is clockwise or counterclockwise.

In some examples, obtaining a plurality of planar images of the region of interest from the original image of the target further includes repeating at least rotating the X-axis about the Y-axis until the X-axis is rotated back to the initial direction. In various examples, the predetermined order is the same as an acquisition order in which the plurality of planar images is obtained. In some examples, the predetermined order is a reverse of an acquisition order in which the plurality of planar images is obtained.

In some embodiments, a medical image displaying device includes an original image acquiring module configured to acquire an original image of a target; a lesion region obtaining module configured to obtain a lesion region in the original image; a region of interest selecting module configured to select a region of interest in the original image based on at least the lesion region, the region of interest including the lesion region; a planar image obtaining module configured to obtain a plurality of planar images of the region of interest from the original image of the target based on at least a predetermined setting; an animated display generating module configured to generate an animated display by grouping the plurality of planar images based on at least a predetermined order; and a displaying module configured to display the animated display related to the region of interest including the lesion region. In some examples, the medical image displaying device is implemented according to at least the medical image displaying device 20 of FIG. 16.

In various examples, the planar image obtaining module is further configured to sequentially obtain the plurality of planar images along a predetermined direction, the plurality of planar images being perpendicular to the predetermined direction. In certain examples, the planar image obtaining module is further configured to: establish a Cartesian coordinate system including an X-axis, a Y-axis, and a Z-axis; perform a maximum intensity projection on the region of interest along the Z-axis in a first direction to obtain a first planar image of the plurality of planar images; rotate the Z-axis from the first direction to a second direction by a predetermined angle; and perform the maximum intensity projection on the region of interest along the Z-axis in the second direction to obtain a second planar image of the plurality of planar images. In some examples, the planar image obtaining module is implemented according to at least the planar image obtaining module 400' of FIG. 18.

In certain embodiments, the planar image obtaining module is further configured to repeat at least rotating the Z-axis by the predetermined angle and performing the maximum intensity projection on the region of interest along the Z-axis to obtain another planar image of the plurality of planar images until the Z-axis is rotated back to the first direction. In some examples, the predetermined order is the same as an acquisition order in which the plurality of planar images is obtained. In certain examples, the predetermined order is a reverse of an acquisition order in which the plurality of planar images is obtained.

In some embodiments, a non-transitory computer-readable medium with instructions stored thereon, that when executed by a processor, perform the processes including: acquiring an original image of a target; obtaining a lesion region in the original image; selecting a region of interest in the original image based on at least the lesion region, the region of interest including the lesion region; obtaining a plurality of planar images of the region of interest from the original image of the target based on at least a predetermined setting; generating an animated display by grouping the plurality of planar images based on at least a predetermined order; and displaying the animated display related to the region of interest including the lesion region. In some examples, the non-transitory computer-readable medium with instructions stored thereon is implemented at least according to the method S100 of FIG. 1 and/or the computer device of FIG. 20.

In certain embodiments, the non-transitory computer-readable medium with instructions stored thereon, that when executed by a processor, perform the process: sequentially obtaining the plurality of planar images along a predetermined direction, the plurality of planar images being perpendicular to the predetermined direction.

In certain embodiments, the non-transitory computer-readable medium with instructions stored thereon, that when executed by a processor, perform the processes: establishing a Cartesian coordinate system including an X-axis, a Y-axis, and a Z-axis; performing a maximum intensity projection on the region of interest along the Z-axis in a first direction to obtain a first planar image of the plurality of planar images; rotating the Z-axis from the first direction to a second direction by a predetermined angle; and performing the maximum intensity projection on the region of interest along the Z-axis in the second direction to obtain a second planar image of the plurality of planar images.

One of ordinary skill in the art is to understand that all or part of the processes of implementing the above embodiments can be completed by a computer program to instruct related hardware, and the computer program can be stored in a non-transitory computer readable storage medium. In the medium, the computer program, when executed, performs the processes of the methods described above. Any reference to a memory, storage, database or other medium used in the various embodiments provided herein may include non-transitory and/or transitory memory. Non-transitory memory can include read only memory (ROM), programmable ROM (PROM), electrically programmable ROM (EPROM), electrically erasable programmable ROM (EEPROM), or flash memory. Transitory memory can include random access memory (RAM) or external cache memory. By way of illustration and not limitation, RAM is available in a variety of formats, such as static RAM (SRAM), dynamic RAM (DRAM), synchronous DRAM (SDRAM), double data rate SDRAM (DDRSDRAM), enhanced SDRAM (ESDRAM), synchronization chain. Synchlink DRAM (SLDRAM), Memory Bus (e.g., Rambus) Direct RAM (RDRAM), Direct Memory Bus Dynamic RAM (DRDRAM), and Memory Bus Dynamic RAM (RDRAM).

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for displaying a medical image, the method comprising:
   acquiring an original image of a target;
   obtaining a lesion region in the original image;
   selecting a region of interest in the original image based on at least the lesion region, the region of interest including the lesion region;
   obtaining a plurality of planar images of the region of interest from the original image of the target based on at least a predetermined setting;
   generating an animated display by grouping the plurality of planar images based on at least a predetermined order; and
   displaying the animated display related to the region of interest including the lesion region;
   wherein the obtaining a plurality of planar images of the region of interest from the original image of the target includes:
      establishing a Cartesian coordinate system including an X-axis, a Y-axis, and a Z-axis;
      performing a maximum intensity projection on the region of interest along the Z-axis in a first direction to obtain a first planar image of the plurality of planar images;
      rotating the Z-axis from the first direction to a second direction by a predetermined angle; and
      performing the maximum intensity projection on the region of interest along the Z-axis in the second direction to obtain a second planar image of the plurality of planar images.

2. The computer-implemented method of claim 1, wherein the obtaining a lesion region in the original image includes:
   obtaining the lesion region by inputting the original image into a neural network trained by a set of training images.

3. The computer-implemented method of claim 1, wherein the obtaining a plurality of planar images of the region of interest from the original image of the target further includes:
   repeating at least rotating the Z-axis by the predetermined angle and performing the maximum intensity projection on the region of interest along the Z-axis to obtain another planar image of the plurality of planar images until the Z-axis is rotated back to the first direction.

4. The computer-implemented method of claim 3, wherein the repeating at least rotating the Z-axis by the predetermined angle and performing the maximum intensity projection on the region of interest along the Z-axis includes:
  fixing the Y-axis, rotating the X-axis about the Y-axis, and performing the maximum intensity projection on the region of interest; and
  fixing the X-axis, rotating the Y-axis about the X-axis, and performing the maximum intensity projection on the region of interest.

5. The computer-implemented method of claim 1, wherein the rotating the Z-axis from the first direction to a second direction by a predetermined angle includes:
  fixing the Y-axis; and
  rotating the X-axis about the Y-axis from an initial direction in a predetermined direction.

6. The computer-implemented method of claim 5, wherein the predetermined direction is clockwise or counterclockwise.

7. The computer-implemented method of claim 5, wherein the obtaining a plurality of planar images of the region of interest from the original image of the target further includes:
  repeating at least rotating the X-axis about the Y-axis until the X-axis is rotated back to the initial direction.

8. The computer-implemented method of claim 1, wherein the predetermined order is the same as an acquisition order in which the plurality of planar images is obtained.

9. The computer-implemented method of claim 1, wherein the predetermined order is a reverse of an acquisition order in which the plurality of planar images is obtained.

10. A medical image displaying device, comprising:
  an original image acquiring module configured to acquire an original image of a target a lesion region obtaining module configured to obtain a lesion region in the original image;
  a region of interest selecting module configured to select a region of interest in the original image based on at least the lesion region, the region of interest including the lesion region;
  a planar image obtaining module configured to obtain a plurality of planar images of the region of interest from the original image of the target based on at least a predetermined setting;
  an animated display generating module configured to generate an animated display by grouping the plurality of planar images based on at least a predetermined order; and
  a displaying module configured to display the animated display related to the region of interest including the lesion region;
  wherein the planar image obtaining module is further configured to:
    establish a Cartesian coordinate system including an X-axis, a Y-axis, and a Z-axis;
    perform a maximum intensity projection on the region of interest along the Z-axis in a first direction to obtain a first planar image of the plurality of planar images;
    rotate the Z-axis from the first direction to a second direction by a predetermined angle; and
    perform the maximum intensity projection on the region of interest along the Z-axis in the second direction to obtain a second planar image of the plurality of planar images.

11. The medical image displaying device of claim 10, wherein the planar image obtaining module is further configured to repeat at least rotating the Z-axis by the predetermined angle and performing the maximum intensity projection on the region of interest along the Z-axis to obtain another planar image of the plurality of planar images until the Z-axis is rotated back to the first direction.

12. The medical image displaying device of claim 10, wherein the predetermined order is the same as an acquisition order in which the plurality of planar images is obtained.

13. The medical image displaying device of claim 10, wherein the predetermined order is a reverse of an acquisition order in which the plurality of planar images is obtained.

14. A non-transitory computer-readable medium with instructions stored thereon, that when executed by a processor, perform the processes comprising:
  acquiring an original image of a target;
  obtaining a lesion region in the original image;
  selecting a region of interest in the original image based on at least the lesion region, the region of interest including the lesion region;
  obtaining a plurality of planar images of the region of interest from the original image of the target based on at least a predetermined setting;
  generating an animated display by grouping the plurality of planar images based on at least a predetermined order; and
  displaying the animated display related to the region of interest including the lesion region;
  wherein the obtaining a plurality of planar images of the region of interest from the original image of the target includes:
    establishing a Cartesian coordinate system including an X-axis, a Y-axis, and a Z-axis;
    performing a maximum intensity projection on the region of interest along the Z-axis in a first direction to obtain a first planar image of the plurality of planar images;
    rotating the Z-axis from the first direction to a second direction by a predetermined angle; and
    performing the maximum intensity projection on the region of interest along the Z-axis in the second direction to obtain a second planar image of the plurality of planar images.

* * * * *